US011413008B2

(12) United States Patent
Dekker et al.

(10) Patent No.: US 11,413,008 B2
(45) Date of Patent: Aug. 16, 2022

(54) INTRALUMINAL ULTRASOUND IMAGING DEVICE COMPRISING A SUBSTRATE SEPARATED INTO A PLURALITY OF SPACED-APART SEGMENTS, INTRALUMINAL ULTRASOUND IMAGING DEVICE COMPRISING A TRENCH, AND METHOD OF MANUFACTURING

(71) Applicant: KONINKLIJKE PHILIPS N.V., Eindhoven (NL)

(72) Inventors: Ronald Dekker, Valkenswaard (NL); Vincent Adrianus Henneken, Utrecht (NL); Marcus Cornelis Louwerse, Nijmegen (NL); Aslihan Arslan Carisey, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 48 days.

(21) Appl. No.: 16/622,416

(22) PCT Filed: Jun. 26, 2018

(86) PCT No.: PCT/EP2018/067006
§ 371 (c)(1),
(2) Date: Dec. 13, 2019

(87) PCT Pub. No.: WO2019/002231
PCT Pub. Date: Jan. 3, 2019

(65) Prior Publication Data
US 2020/0205776 A1 Jul. 2, 2020

Related U.S. Application Data

(60) Provisional application No. 62/679,134, filed on Jun. 1, 2018, provisional application No. 62/527,143, filed on Jun. 30, 2017.

(51) Int. Cl.
*A61B 8/12* (2006.01)
*A61B 8/00* (2006.01)
*B06B 1/02* (2006.01)

(52) U.S. Cl.
CPC ............... *A61B 8/12* (2013.01); *A61B 8/445* (2013.01); *A61B 8/4488* (2013.01);
(Continued)

(58) Field of Classification Search
CPC ......... A61B 8/12; A61B 8/445; A61B 8/4488; A61B 8/4494; A61B 8/56; B06B 1/0292
See application file for complete search history.

(56) References Cited

U.S. PATENT DOCUMENTS 6,776,763 B2   8/2004 Nix
7,226,417 B1   6/2007 Eberle
(Continued)

FOREIGN PATENT DOCUMENTS

WO   2016008690 A1   1/2016
WO   2019110334 A1   6/2019
(Continued)

OTHER PUBLICATIONS

Franz Laermer, Sami Franssila, Lauri Sainiemi, Kai Kolari, Chapter 21—Deep Reactive Ion Etching, Editor(s): Markku Tilli, Teruaki Motooka, Veli-Matti Airaksinen, Sami Franssila, Mervi Paulasto-Kröckel Veikko Lindroos, In Micro and Nano Technologies, Handbook of Silicon Based MEMS Materials an Technologies (Second Edition) , William Andrew Publishing, 2015, pp. 444-469.*
(Continued)

*Primary Examiner* — Ashley K Buran
*Assistant Examiner* — Sean V Blinder

(57) ABSTRACT

An intraluminal ultrasound imaging device includes a flexible elongate member configured to be positioned within a body lumen of a patient. The flexible elongate member
(Continued)

includes a proximal portion and a distal portion. The device also includes an ultrasound imaging assembly disposed at the distal portion of the flexible elongate member. The ultrasound imaging assembly is configured to obtain imaging data of the body lumen. The ultrasound imaging assembly includes a transducer array including a substrate, a silicon oxide layer disposed over the substrate, and a plurality of rows of micromachined ultrasound transducer elements disposed on the silicon oxide layer. Two of the plurality of rows of micromachined ultrasound transducer elements are spaced apart by a trench formed by etching through a screen formed in the silicon oxide layer. Associated devices, systems, and methods are also provided.

18 Claims, 18 Drawing Sheets

(52) U.S. Cl.
CPC .............. *A61B 8/4494* (2013.01); *A61B 8/56* (2013.01); *B06B 1/0292* (2013.01)

(56) References Cited

U.S. PATENT DOCUMENTS

| | | | |
|---|---|---|---|
| 7,846,101 B2 | 12/2010 | Eberle | |
| 10,175,206 B2* | 1/2019 | Rothberg | ............. A61B 8/4483 |
| 10,177,139 B2* | 1/2019 | Rothberg | ............ B81C 1/00158 |
| 2008/0259725 A1 | 10/2008 | Bayram | |
| 2010/0125198 A1* | 5/2010 | Thapliyal | ............. A61B 8/4494 600/439 |
| 2010/0280388 A1 | 11/2010 | Huang | |
| 2011/0254109 A1 | 10/2011 | Ossmann | |
| 2013/0310679 A1 | 11/2013 | Natarajan | |
| 2014/0276087 A1* | 9/2014 | Corl | ..................... B06B 1/0629 600/467 |
| 2014/0307528 A1 | 10/2014 | Dekker | |
| 2015/0107362 A1 | 4/2015 | Shin | |

FOREIGN PATENT DOCUMENTS

| | | |
|---|---|---|
| WO | 2019110698 A1 | 6/2019 |
| WO | 2019110699 A1 | 6/2019 |
| WO | 2019110776 A1 | 6/2019 |

OTHER PUBLICATIONS

Pappalardo, Massimo, et al. "Micromachined ultrasonic transducers." Piezoelectric and Acoustic Materials for Transducer Applications. Springer, Boston, MA, 2008. 453-478.*
International Search Report & Written Opinion of PCT/EP2018/067006, dated Sep. 13, 2018.

* cited by examiner

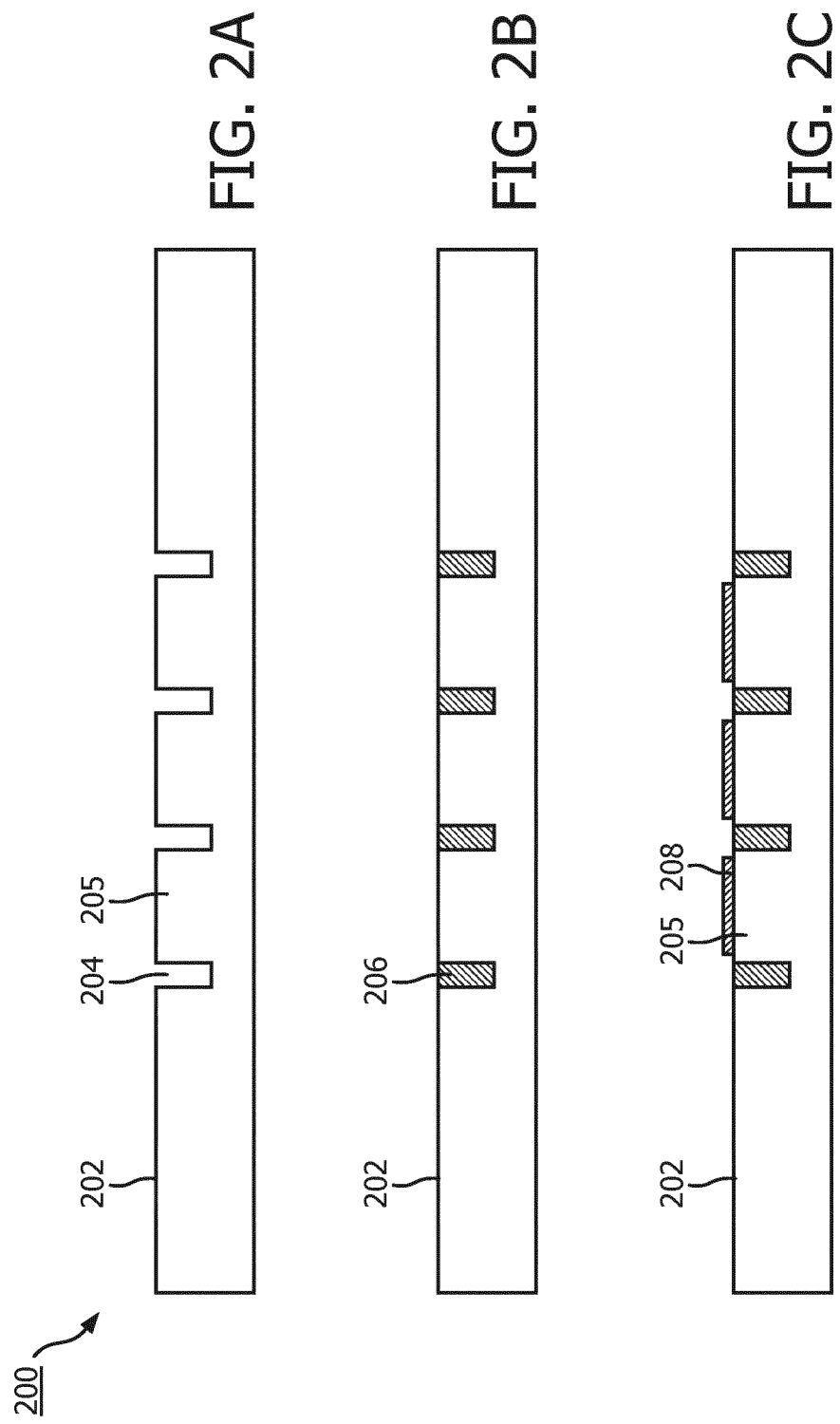

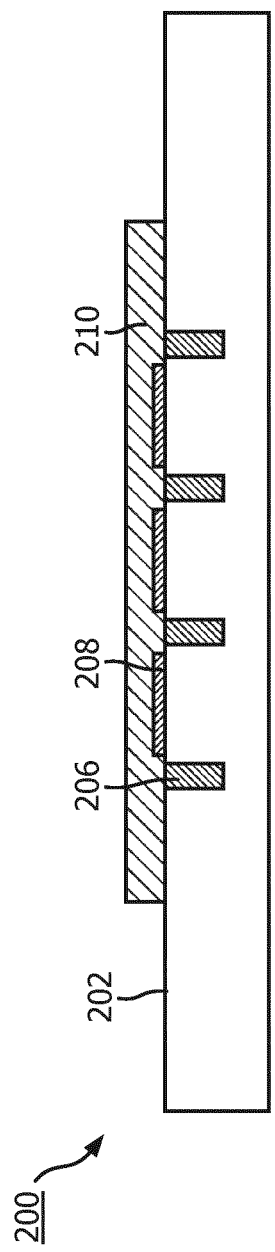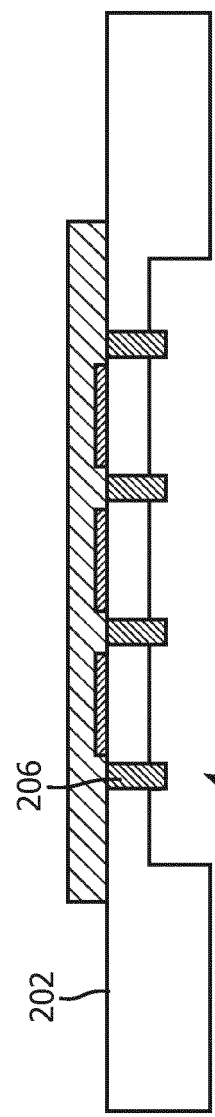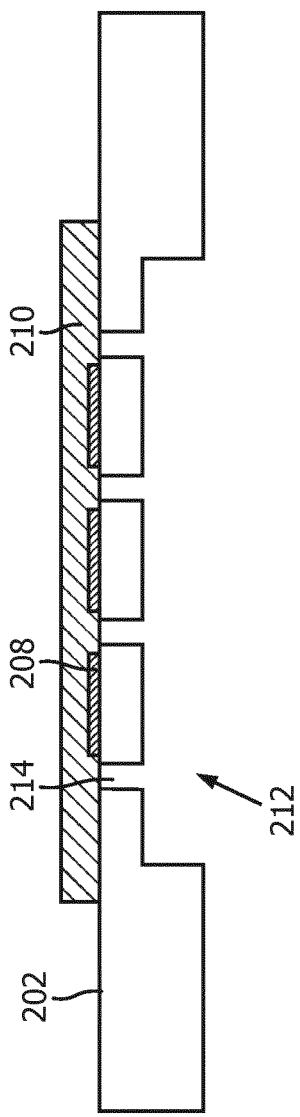

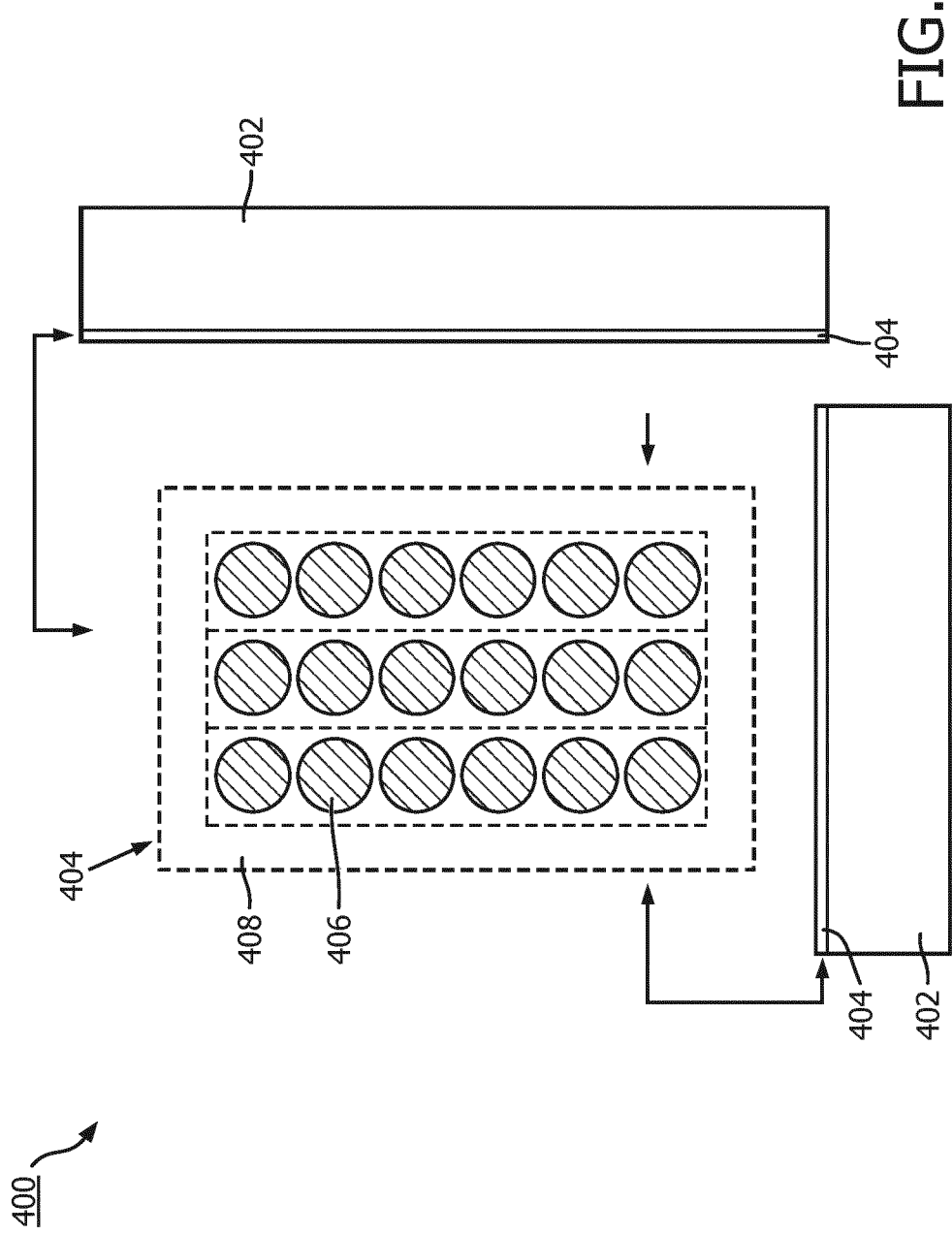

INTRALUMINAL ULTRASOUND IMAGING DEVICE COMPRISING A SUBSTRATE SEPARATED INTO A PLURALITY OF SPACED-APART SEGMENTS, INTRALUMINAL ULTRASOUND IMAGING DEVICE COMPRISING A TRENCH, AND METHOD OF MANUFACTURING

CROSS-REFERENCE TO RELATED APPLICATIONS

The present application claims priority to and the benefit of U.S. Provisional Application No. 62/527,143, filed Jun. 30, 2017, and U.S. Provisional Application No. 62/679,134, filed Jun. 1, 2018, the entireties of which are incorporated by reference.

TECHNICAL FIELD

The present disclosure relates generally to microelectromechanical systems (MEMS) and, in particular, to an ultrasound transducer array and method of fabricating the same. For example, in some embodiments, the method of fabricating an ultrasound transducer array can include forming a buried trench without having to fill the trench with temporary filling materials.

BACKGROUND

The Flex-to-Rigid (F2R) technology is a manufacturing platform that enables fabrication of miniature and complex electromechanical components, such as sensors and imaging transducers in large numbers on tips of minimally invasive catheters and guide wires. MEMS devices, such as a capacitive micromachined ultrasound transducer (CMUT) array or a piezoelectric micromachined ultrasound transducer (PMUT) array, are first fabricated on a semiconductor substrate and then transferred to a flexible substrate. Utilizing the F2R technology, the CMUT or PMUT array can be formed in a variety of sizes on the semiconductor substrate, along with application specific integrated circuit (ASIC) and passive components. One of the most common semiconductor substrates is a silicon substrate. As silicon is a good conductor of sound waves, cross talk between CMUT or PMUT transducers can be a problem. A solution to the cross talk problem is forming the ultrasound transducers on islands isolated by buried trenches.

Conventionally, forming a buried trench to isolate micromachined ultrasound transducers requires filling trenches with a sacrificial material, such as a polymer, and removing the sacrificial material in a later step, such as a step of selective etching from a backside of the semiconductor substrate. The sacrificial material temporarily filled in the trench has a tendency to shrink during curing or hardening and can cause stress in the semiconductor substrate, resulting in undesirable bowing or warping of the semiconductor substrate. In addition, as it is desirable to minimize the width of the trench to maximize scanner areas for micromachined ultrasound transducers, it becomes increasingly difficult to fill the ever smaller trenches with the sacrificial material.

SUMMARY

Embodiments of the present disclosure provide a method of fabricating buried trenches in a microelectromechanical system (MEMS) device, such as an ultrasound transducer element that obtains image data of a body lumen of a patient. An exemplary method includes forming a screen out of silicon oxide or metal lines over a region on a semiconductor substrate and then etching the region with deep reactive ion etching (DRIE) and using the screen as an etch mask. By increasing cycle times of the DRIE, a substantially vertical trench can be formed in the region while the screen remains in place. A non-conformal layer is then deposited over the semiconductor substrate to close holes in the screen without filling the trench, thereby forming a buried trench.

In an exemplary embodiment, an intraluminal ultrasound imaging device is provided. The device includes a flexible elongate member configured to be positioned within a body lumen of a patient, the flexible elongate member comprising a proximal portion and a distal portion; and an ultrasound imaging assembly disposed at the distal portion of the flexible elongate member, the ultrasound imaging assembly configured to obtain imaging data of the body lumen, the ultrasound imaging assembly comprising a transducer array comprising: a substrate separated into a plurality of spaced-apart segments, a hard mask layer disposed over the substrate, and a plurality of rows of transducer elements disposed on the hard mask layer, wherein at least one sidewall of each of the plurality of spaced-apart segments of the substrate comprises wave-like features propagating along two directions perpendicular to one another. The plurality of spaced-apart segments may be fully and/or partially separated from one another.

In some embodiments, the substrate comprises silicon, and the hard mask layer comprises silicon oxide. In some embodiments, each of the plurality of rows of transducer elements comprises capacitive micromachined ultrasound transducer (CMUT) elements or piezoelectric micromachined ultrasound transducer (PMUT) elements. In some embodiments, the ultrasound imaging assembly further comprises a flexible interconnect, two of the plurality of rows of transducer elements are spaced apart from one another by a trench, the flexible interconnect spans over the trench, and the flexible interconnect comprises a surface including an array of recesses. In some embodiments, the device further includes a tubular member, wherein the flexible interconnect and the transducer array positioned around the tubular member.

In an exemplary embodiment, a method of manufacturing an intraluminal ultrasound imaging device is provided. The method includes providing a substrate comprising a hard mask on a first side of the substrate; forming a first plurality of holes through the hard mask in a first area; etching the substrate through the first plurality of holes, thereby forming a trench; depositing a material layer over first plurality of holes; forming a plurality of ultrasound transducer elements in a second area adjacent to the first area; and forming a flexible layer over the substrate in the first and second areas.

In some embodiments, the substrate is a silicon-on-insulator (SOI) substrate. In some embodiments, providing the substrate comprises forming the hard mask on the first side of the substrate. In some embodiments, forming the first plurality of holes through the hard mask in the first area comprises etching the hard mask using a metal layer as an etch mask, the metal layer including a second plurality of holes. In some embodiments, etching the substrate through the first plurality of holes comprises etching the substrate through the first plurality of holes using deep reactive ion etching (DRIE). In some embodiments, depositing the material layer over the first plurality of holes comprises depositing the material layer using plasma-enhanced chemical vapor deposition (PECVD). In some embodiments, forming the plurality of ultrasound transducer elements in the second area comprises forming capacitive micromachined ultrasound transducer (CMUT) elements or piezoelectric micromachined ultrasound transducer (PMUT) elements. In some embodiments, the method further comprises: forming an opening on a second side of the substrate to expose the trench. In some embodiments, the method further comprises: removing, from the second side through the opening, the material layer and the hard mask exposed in the trench. In some embodiments, the method further comprises: planarizing the material layer deposited over the first plurality of holes.

In an exemplary embodiment, an intraluminal ultrasound imaging device is provided. The device includes a flexible elongate member configured to be positioned within a body lumen of a patient, the flexible elongate member comprising a proximal portion and a distal portion; and an ultrasound imaging assembly disposed at the distal portion of the flexible elongate member, the ultrasound imaging assembly configured to obtain imaging data of the body lumen, the ultrasound imaging assembly comprising a transducer array comprising: a substrate, a silicon oxide layer disposed over the substrate, and a plurality of rows of micromachined ultrasound transducer elements disposed on the silicon oxide layer, wherein two of the plurality of rows of micromachined ultrasound transducer elements are spaced apart by a trench formed by etching through a screen formed in the silicon oxide layer.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 2A, 2B, 2C, 2D, 2E and 2F are diagrammatic cross-sectional views of a semiconductor substrate in a fabrication process, according to an embodiment of the present disclosure.

FIGS. 4A, 4B, 4C, 4D, 4E, 4F, and 4G are diagrammatic top views and cross-sectional views of a semiconductor substrate in different operations of an embodiment of the method in FIG. 3, according to an embodiment of the present disclosure.

DETAILED DESCRIPTION

Figure 1A:
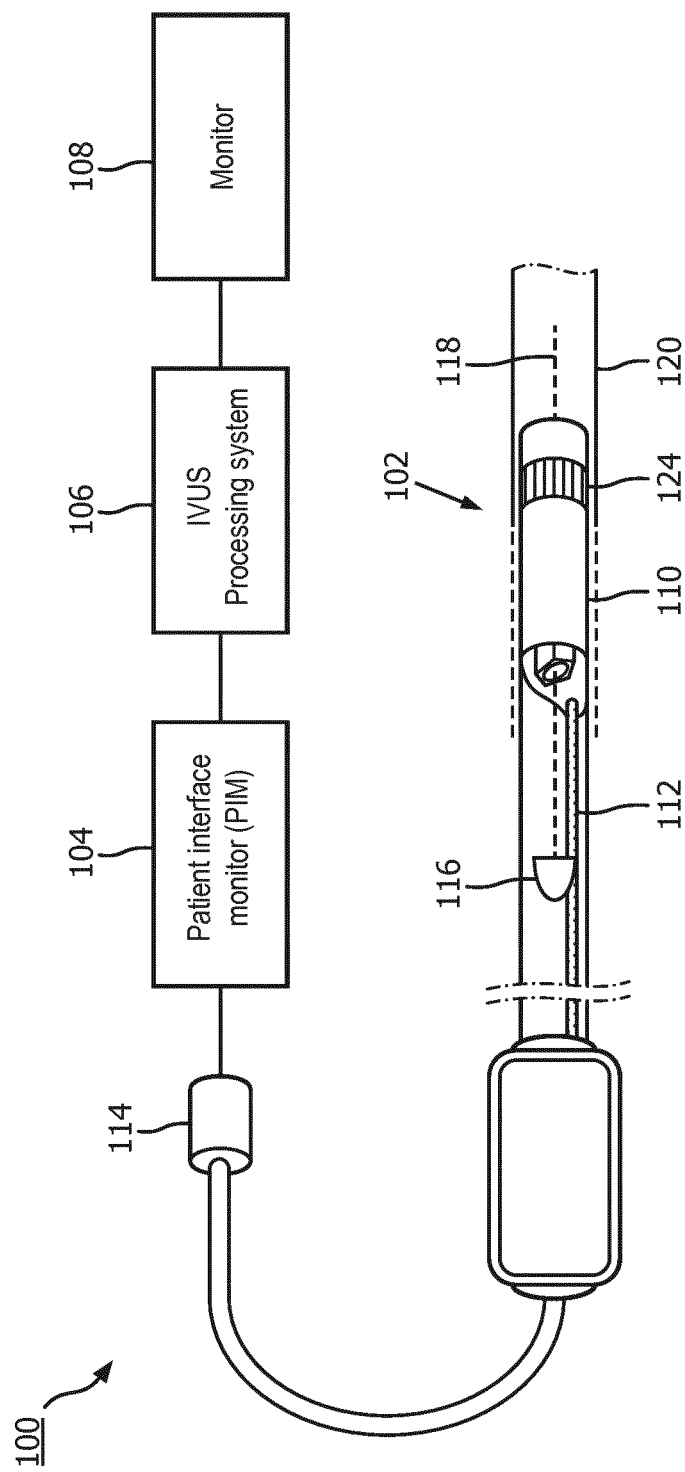
FIG. 1A is a diagrammatic schematic view of an intraluminal ultrasound imaging system, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the formation of the buried trench is described in terms of intravascular ultrasound imaging, it is understood that it is not intended to be limited to this application. The formation of the buried trench is equally well suited to any application requiring a buried trench. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a diagrammatic schematic view of an intraluminal ultrasound imaging system 100, according to aspects of the present disclosure. For example, the system 100 can be intravascular ultrasound (IVUS) imaging system. The intraluminal ultrasound imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to one or more control logic integrated circuits included in the scanner assembly 110 to select the particular transducer array element(s) to be used for transmit and receive, (2) providing the transmit trigger signals to the one or more control logic integrated circuits included in the scanner assembly 110 to activate the transmitter circuitry to generate an electrical pulse to excite the selected transducer array element(s), and/or (3) accepting amplified echo signals received from the selected transducer array element(s) via amplifiers included on the one or more control logic integrated circuits of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Generally, the system 100 and/or the device 102 can be used in any suitable lumen of a patient body. In that regard, the system 100 can be an intraluminal ultrasound imaging system, and the device 102 can be an intraluminal ultrasound imaging device. The system 100 and/or the device 102 can be referenced as an interventional device, a therapeutic device, a diagnostic device, etc. The device 102 can be sized and shaped, structurally arranged, and/or otherwise configured to be positioned within the vessel or lumen 120. Lumen or vessel 120 may represent fluid filled or surrounded structures, both natural and man-made. The lumen or vessel 120 may be within a body of a patient. The vessel 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 1B:
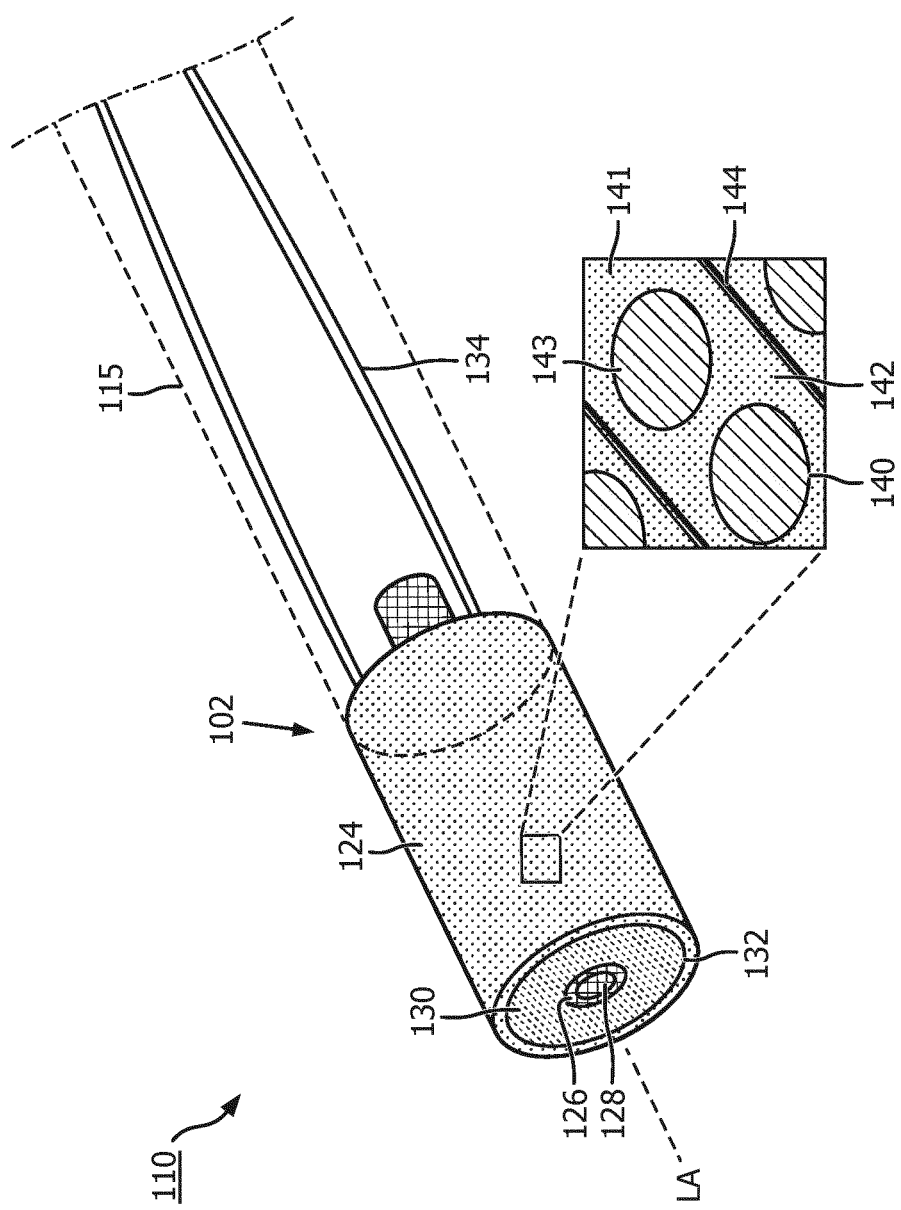
FIG. 1B is a diagrammatic perspective view of an intraluminal ultrasound imaging device including an ultrasound scanner assembly, according to an embodiment of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 134 (as shown in FIG. 1B). It is understood that any suitable gauge wire can be used for the conductors 134. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

FIG. 1B is a diagrammatic perspective view of the intraluminal imaging device 102, including the ultrasound scanner assembly 110 in FIG. 1A. In some embodiments, the ultrasound scanner assembly 110 can be disposed at a distal portion of a flexible elongate member 115 of the device 102. The flexible elongate member 115 is sized and shaped, structurally arranged, and/or otherwise configured to be positioned within a body lumen of a patient. The scanner assembly 110 obtains ultrasound imaging data associated with the body lumen while the device 102 is positioned within the body lumen. As shown in FIG. 1B, the scanner assembly 110 may include a transducer array 124 positioned around a longitudinal axis LA of the device 102. In some instances, the array 124 is disposed in a rolled or cylindrical configuration around a tubular member 126. In some instances, the scanner assembly 110 can include a diameter between about 0.8 mm and about 1.6 mm, such as 1.2 mm. The tubular member 126 can also be referred to as a support member, a unibody, or a ferrule. In some implementations, the tubular member 126 can include a lumen 128. The lumen 128 can be sized and shaped to receive a guide wire, such as the guide wire 118 shown in FIG. 1A. The device 102 can be configured to be moved along or ride on the guide wire 118 to a desired location within the physiology of the patient. In those implementations, the lumen 128 can be referred to as a guide wire lumen 128. In some embodiments, the scanner assembly 110 may also include a backing material 130 between the transducer array 124 and the tubular member 126. In that regard, the tubular member 126 can include stands that radially space the transducer array 124 from the body of the member 126. The backing material 130 can be disposed within the radial space between the tubular member 126 and the array 124. The backing material 130 serves as an acoustic damper to reduce excessive vibration and to improve axial resolution of the resulting ultrasound imaging device.

As shown in the enlarged view of a region of the transducer array 124, the transducer array 124 can include a plurality of rows of ultrasound transducer elements 140 (or a plurality of rows of acoustic elements 140) fabricated on a semiconductor substrate 132. The semiconductor substrate 132 is divided into a plurality of islands 141 spaced apart from one another and/or separated by buried trenches 144. That is, the substrate 132 is separated into a plurality of spaced-apart segments 141. The spaced-apart segments 141 of the substrate 132 may be fully separated from one another, partially separated from one another, and/or a combination of fully and partially separated from one another. The divided islands 141 of the semiconductor substrate 132 are coupled to a common flexible interconnect 142. The flexible interconnect 142 can extend around the elements 140 as well as across and/or over the trenches 144. The flexible interconnect 142 can include holes aligned with a diaphragm or movable membrane 143 of the transducer elements 140. In such instances, the interconnect 142 does not completely cover the islands 141. The interconnect 142 can cover portions of the islands 141 that do not include the diaphragm or movable membrane 143 of the transducer elements 140. In some embodiments, the interconnect 142 completely covers the islands 141, including the diaphragm or movable membrane 143 of the transducer elements 140, such as when the flexible interconnect 142 also comprises an acoustic matching layer. The trenches 144 isolate the islands 141, which allows islands to be orientated at different angles, such as when the array 124 is positioned around the longitudinal axis LA of the device 102. The flexible interconnect 142 is made of polymer material, such as polyimide (for example, KAPTON™ (trademark of DuPont)), and can be considered a flexible substrate. Other suitable polymer materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). As the transducer array 124 is first fabricated on the semiconductor substrate 132, which is rigid, and then a flexible substrate (i.e. the flexible interconnect 142) is positioned over the transducer array 124, the transducer array 124 is fabricated using flexible-to-rigid (F2R) technology. The buried trenches 144 are positioned under the flexible interconnect 142 and form the fold lines when the transducer array 124 is rolled around the tubular member 126.

The scanner assembly 110 may include one or more control logic integrated circuits (IC), such as application specific integrated circuits (ASICs). In some embodiments, the one or more control logic ICs can be mounted on the imaging assembly 110 longitudinally proximal to the transducer array 124. In some other embodiments, the one or more control logic ICs can be disposed between the rolled-around transducer array 124 and the tubular member 126. Aspects of an intraluminal imaging device, including various techniques of transforming the transducer array 124 from a flat configuration to a cylindrical or rolled-around configuration, are disclosed in one or more of U.S. Pat. Nos. 6,776,763, 7,226,417, U.S. Provisional App. No. 62/596, 154, filed Dec. 8, 2017, U.S. Provisional App. No. 62/596, 141, filed Dec. 8, 2017, U.S. Provisional App. No. 62/596, 300, filed Dec. 8, 2017, U.S. Provisional App. No. 62/596, 205, filed Dec. 8, 2017, each of which is hereby incorporated by reference in its entirety.

In some embodiments, the transducer elements of the array 124 and/or the controller ICs can be positioned in an annular configuration, such as a circular configuration or in a polygon configuration, around the longitudinal axis LA of the support member 126. It will be understood that the longitudinal axis LA of the support member 126 may also be referred to as the longitudinal axis of the scanner assembly 110, the flexible elongate member 115, and/or the device 102. For example, a cross-sectional profile of the imaging assembly 110 at the transducer element array 124 and/or the controller ICs can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of controller ICs may be used for controlling the plurality of ultrasound transducer elements of the array 124 to obtain imaging data associated with the body lumen 120.

In some embodiments, the substrate 132 may be formed of a semiconductor material. Each of the ultrasound transducer elements 140 in the transducer array 124 can be a micromachined ultrasound transducer, such as a capacitive micromachined ultrasound transducer (CMUT) or a piezoelectric micromachined ultrasound transducer (PMUT). While each of the ultrasound transducer elements 140 is illustrated as being circular in shape, it should be understood that each of the ultrasound transducer elements 140 can be in any shape.

The buried trench 144 can be fabricated using a process demonstrated in FIGS. 2A-2F. Referring now to FIG. 2A, shown therein is a MEMS device 200. The MEMS device 200 can be fabricated on a semiconductor substrate 202, such as a silicon (Si) substrate or a germanium (Ge) substrate. In some embodiments, the semiconductor substrate 202 may include a compound semiconductor such as silicon carbide (SiC), silicon germanium (SiGe), silicon germanium carbide (SiGeC). In some implementations, the semiconductor substrate may include a silicon on insulator (SOI) substrate. To fabricate the buried trenches 144, trenches 204 can be formed on the semiconductor substrate 202 by dry etching, including reactive ion etching (RIE), or wet etching techniques. In some embodiments, the trenches 204 can be formed using deep trench reactive ion etching (DRIE). The DRIE utilizes a succession of short etch and passivation cycles to produce a substantially straight sidewall. The trenches 204 define a plurality of islands 205 on the semiconductor substrate 202. In some embodiments, each of the plurality of islands 205 includes a width between about 50 μm and about 90 μm, such as about 70 μm, and a thickness between about 20 μm and about 60 μm, such as 40 μm.

As shown in FIG. 2B, the trenches 204 can then be filled with a sacrificial polymer material 206, such as a polymer. For example, the sacrificial polymer material may include polyimide or benzocyclobutene (BCB). In some embodiments, the sacrificial polymer material 206 may be deposited on the substrate 202 using a spin coating technique. After the sacrificial polymer material 206 is coated on the substrate 202, the substrate 202 can be placed in an oven or irradiated with ultraviolet light to cure the sacrificial polymer material 206 and to drive away the solvent in the sacrificial polymer material 206. Once the sacrificial polymer material 206 is cured, it can be planarized by a planarization process, such as chemical mechanical polishing (CMP). MEMS components, such as micromachined ultrasound transducer elements 208, are then fabricated on each of the islands 205. In some implementations, each of the micromachined ultrasound transducer elements 208 can include a diaphragm and a drumhead. As shown in FIG. 2D, to transfer the MEMS device 200 onto a flexible substrate, a flexible interconnect 210 is formed over the semiconductor substrate 202, including over the micromachined ultrasound transducer elements 208 and the trench-filling sacrificial material 206. Reference is now made to FIG. 2E, the semiconductor substrate 202 is then etched from a backside to expose the sacrificial polymer material 206 by dry etching, including reactive ion etching (RIE), or wet etching. In some embodiments represented in FIG. 2E, because of high etching selectivity between the sacrificial polymer material 206 and the semiconductor substrate 202, the sacrificial polymer material 206 remains largely unetched. As illustrated in FIG. 2F, the buried trenches 214 are formed after the sacrificial polymer material 206 is removed from the semiconductor substrate 202.

The process illustrated in FIGS. 2A-2F is not entirely satisfactory. Firstly, the polymers limit the temperature budget that is allowed after filling of the trenches. Furthermore, the sacrificial polymer material 206 can shrink during curing, thereby exerting stress on the semiconductor substrate 202. This stress can cause unacceptable bowing or warping of the semiconductor substrate 202. In addition, as the array density of the MEMS device 200 increases, the trenches 204 can become narrower. The narrower trenches 204 can make it difficult for the sacrificial polymer material 206 to fill the trenches 204 in spin coating processes, leaving behind undesirable voids. At the backside etching step shown in FIG. 2E, such voids may lead to uneven etching of the islands and therefore, deteriorated performance of the MEMS device 200.

Figure 3:
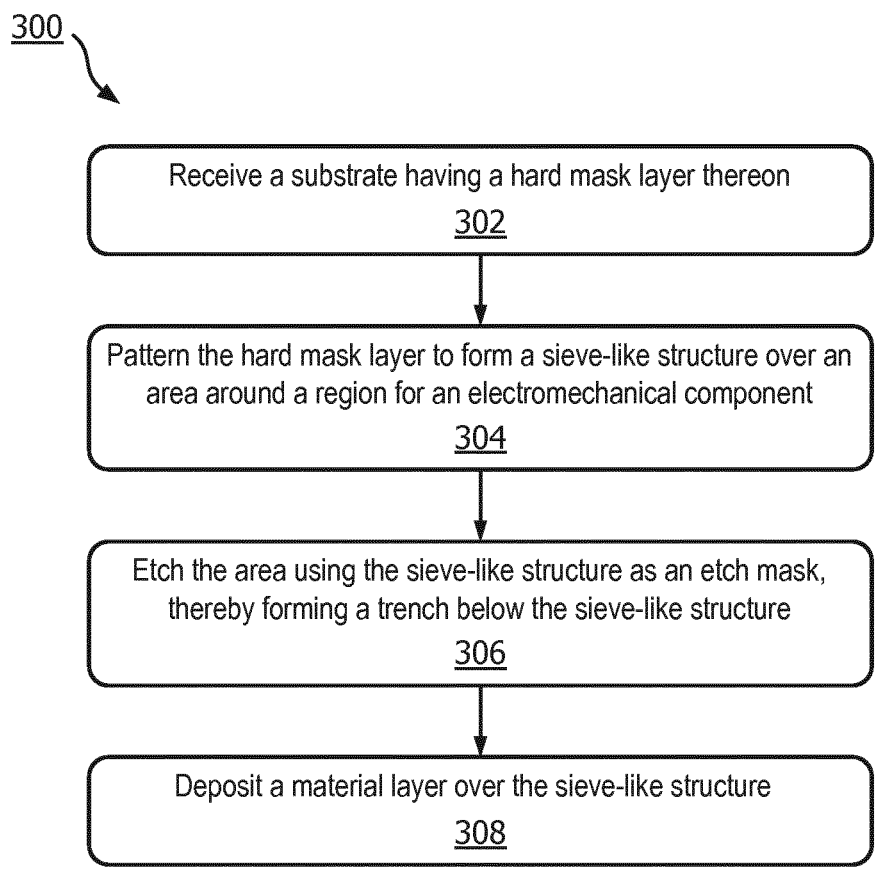
FIG. 3 is a flow chart of a method of fabricating a buried trench on a semiconductor substrate, according to an embodiment of the present disclosure.

Referring now to FIG. 3, shown therein is a flowchart of a method 300 for fabricating buried trenches without use of a sacrificial material, such as the sacrificial polymer material 206 in FIG. 2B. The method 300 can be a method of a manufacturing an intraluminal ultrasound imaging device. The method 300 is merely an example, and is not intended to limit the present disclosure beyond what is explicitly recited in the claims. Additional operations can be provided before, during, and after the method 300, and some operations can be replaced, eliminated, or moved around for additional embodiments of the method.

The method 300 can be applied in multiple different process settings. For example, the method 300 can be applied in a stand-alone setting where a MEMS device 400 (such as an ultrasound transducer array 400) is fabricated alone on a semiconductor substrate 402 as shown in FIGS. 4A-4G, as well as in an integrated setting where a MEMS device 500 (such as an ultrasound transducer array 500) is fabricated along with other electrical components as shown in FIGS. 5A-5I.

Reference is now made to FIG. 4A. In the stand-alone setting, the method 300 begins at block 302 where a semiconductor substrate 402 is received. The semiconductor substrate 402 can be a silicon (Si) substrate or a germanium (Ge) substrate. In some embodiments, the semiconductor substrate 402 may include a compound semiconductor such as silicon carbide (SiC), silicon germanium (SiGe), silicon germanium carbide (SiGeC). The semiconductor substrate 402 includes a hard mask 404 thereon. In some embodiments, the hard mask 404 may be formed of silicon oxide ($SiO_2$) using chemical vapor deposition (CVD). In some implementations, the hard mask 404 may be formed of silicon nitride (SiN) or silicon oxynitride (SiON). In some instances, the hard mask 404 has a thickness ranging between 0.5 μm and 2 μm, including, for example, 1 μm. As illustrated in the top view in FIG. 4A, the semiconductor substrate 402 includes circular-shaped areas 406 that are projected areas for micromachined ultrasound transducer elements, such as CMUTs. The areas 406 are disposed on islands surrounded by isolation areas 408 where isolation features, such as buried trenches are to be formed. In some instances, the semiconductor substrate 402 can be a silicon-on-insulator (SOI) substrate having a buried oxide (BOX) layer of a well-defined thickness.

Figure 4B:
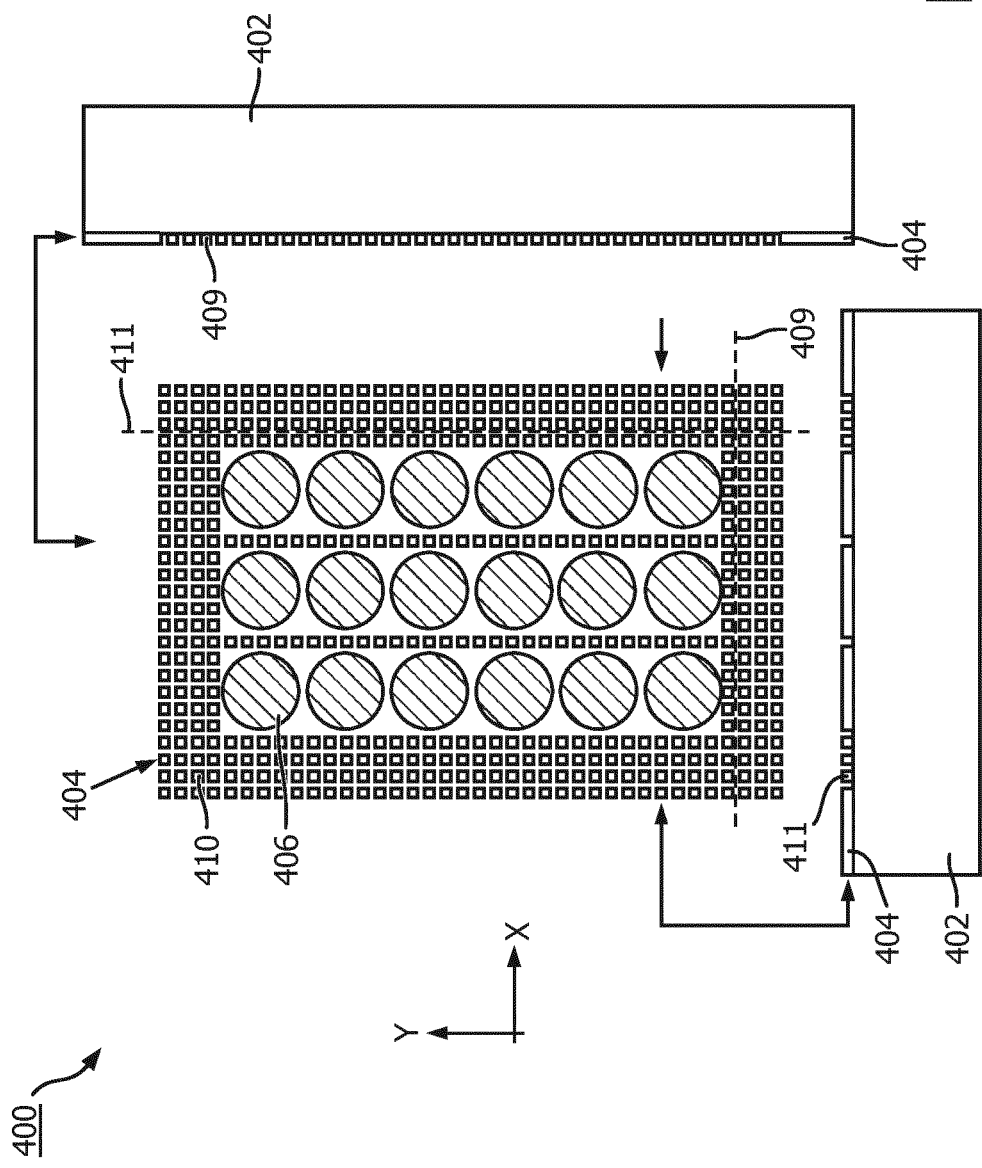

Referring now to FIG. 4B, the method 300 proceeds to block 304 where the hard mask, such as the hard mask 404 in FIG. 4B, is patterned to form a screen over the isolation areas 408 around the areas 406 where the micromachined ultrasound transducer elements are to be fabricated. In the embodiments represented in FIG. 4B, arrays of rectangular holes 410 (or holes 410) are formed through the hard mask 404, leaving behind substantially straight hard mask lines 409 that extend along the X direction and substantially straight hard mask lines 411 that extend the Y direction on the top-facing surface. The hard mask lines 409 and the hard mask lines 411 form a screen (or a grid) with rectangular holes 410 exposing the underneath the semiconductor substrate 402. In some implementations, each of the rectangular holes 410 are substantially square in shape and includes a width/length between about 0.5 μm and about 2 μm, including, for example, about 1 μm. In these implementations, the array of rectangular holes 410 includes a pitch that is about two times of the width/length of the hole. For example, when the width/length of each of the rectangular holes 410 is about 1 μm, the pitch of the array of rectangular holes 410 is about 2 μm. While the holes 410 are rectangular in FIG. 4B, the present disclosure is not so limited. In some embodiments, the holes 410 can be of any shape, including circular, triangular, hexagonal, polygonal, elongated slit, or irregular shapes. The advantages of the embodiments of the present disclosure can be present as long as the hard mask 404 is patterned into a screen with through holes formed therein.

Figure 4C:
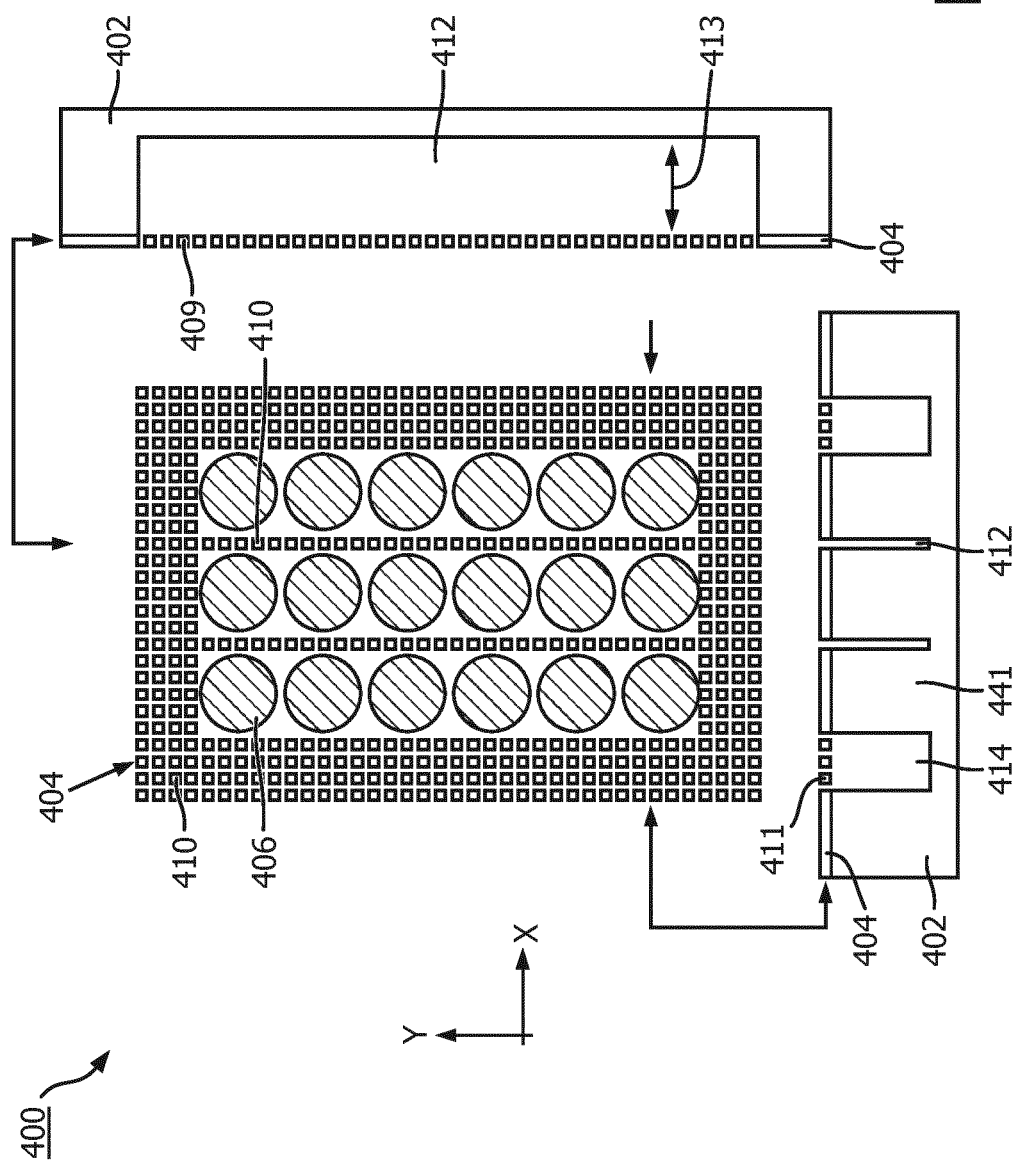

Referring now to FIG. 4C, the method 300 proceeds to block 306 where the isolation areas 408 are etched using the screen as an etch mask to form trenches 412 and 414. In some embodiments, the operations at block 306 are performed using an etching chemistry that has etching selectivity with respect to the semiconductor substrate 402. That way, the material of the semiconductor substrate 402 can be selectively etched without substantially damaging the screen formed of the hard mask 404. In some implementations, the operations at block 306 are performed using a DRIE process that preferentially etches the silicon substrate exposed by the screen without substantially damaging the screen formed of silicon oxide. In some embodiments, a cycle time for etch cycles of the DRIE process can be increased to increase the undercut, so as to etch the substrate material under the hard mask lines 409 and 411. The operations of block 306 create trenches 412 and 414 that are buried under the screen. In that regard, trenches 412 and 414 are created while the screen formed in the hard mask 404 remains positioned over trenches 412 and 414. That is, the hard mask 404 positioned over the trenches 412 and 414 is not completely etched through while the trenches 412 and 414 are formed. In that regard, the trenches 412 and 414 can be referenced as buried trenches in that trenches are positioned under the screen formed in the hard mask 404. The trenches 412 and 414 can include a depth 413. In some instances, the depth 413 can be between about 30 μm and 50 μm, including, for example, about 40 μm. In cases in which an SOI substrate is used, the depth of the trenches is equal to the thickness of the top silicon layer of the SOI substrate. In the embodiments represented in FIG. 4C, the trenches 412 and 414 are straight along the Y direction. In some embodiments, the trenches 412, 414 are linear. In some other embodiments, the trenches 412 and 414 are curved. In still some other embodiments, the trenches 412 and 414 are serpentine in shape. The trenches 412, 414 can track the profiles of the areas 406 where the micromachined ultrasound transducer elements will be formed. Curved trenches may be used to make, e.g. circular islands, which fit on the tip of a catheter. Serpentine catheters may be used to achieve an optimal packing density of circular ultrasound transducers. The trenches 412 and 414 define islands 441 in the substrate 402.

Figure 4D:
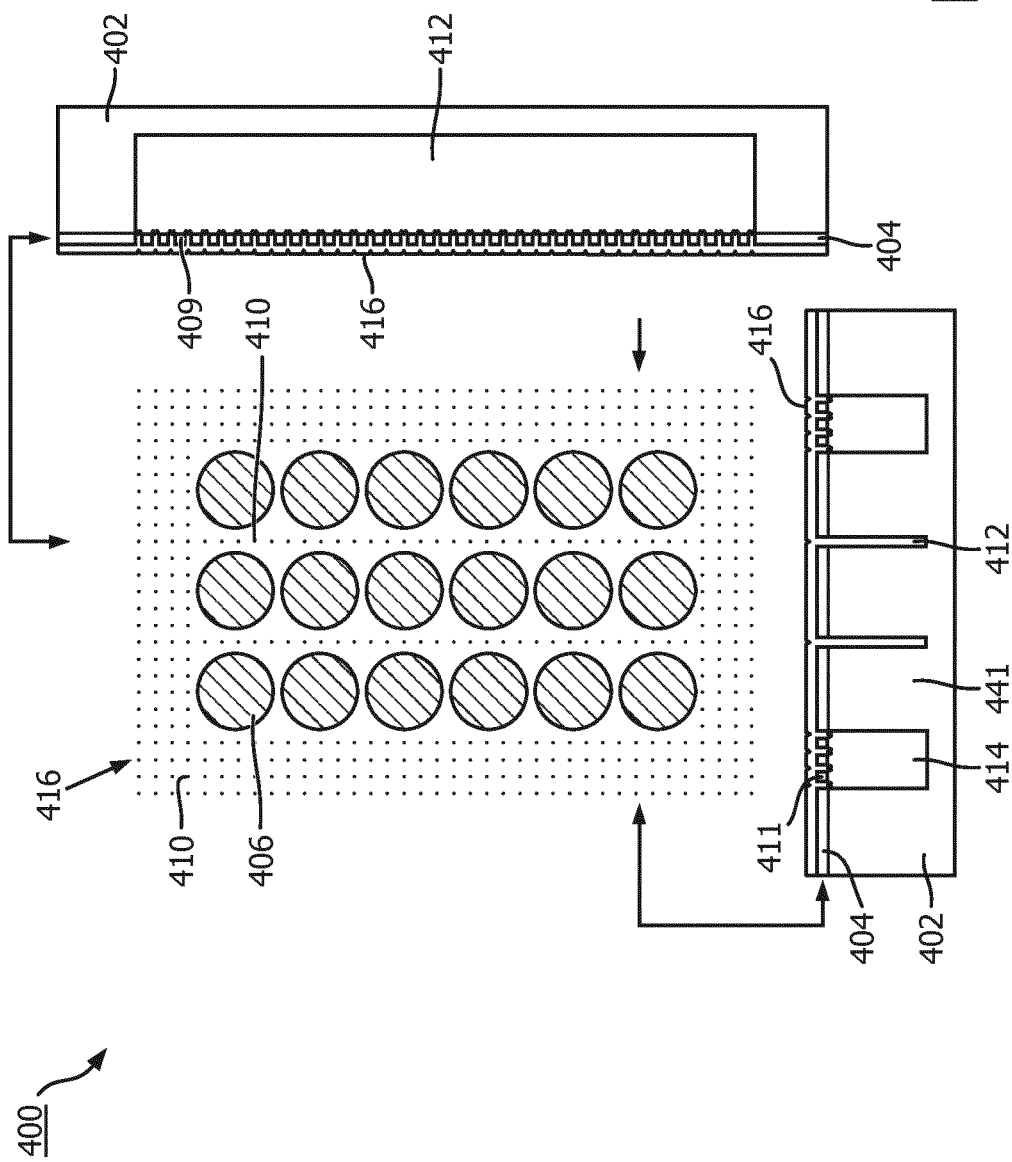

Referring now to FIG. 4D, the method 300 proceeds to block 308 where a material layer 416 is deposited over the screen to close the through holes 410. In some embodiments, the material layer 416 is formed over the screen using a process that does not fill the trenches 412 and 414 with the material layer 416. In some implementations, the material layer 416 can be a silicon oxide layer deposited using plasma-enhanced chemical vapor deposition (PECVD) to close the holes 410. Put differently, the operations of block 308 lay the material layer 416 over the screen to completely cover the trenches 412 and 414 without filling them. The operations at block 308 therefore leave trenches 412 and 414 buried under the screen and the material layer 416. In some instances, while the material layer 416 covers and closes the through holes 410, the material layer 416 can include recesses that correspond to locations of the through holes 410. In the embodiments represented in FIG. 4D, the array of holes 410 can cause the material layer 416 to have a corresponding array of recesses. In implementations where the holes 410 are elongated slits, the material layer 416 can have corresponding array of elongated recesses.

Figure 4E:
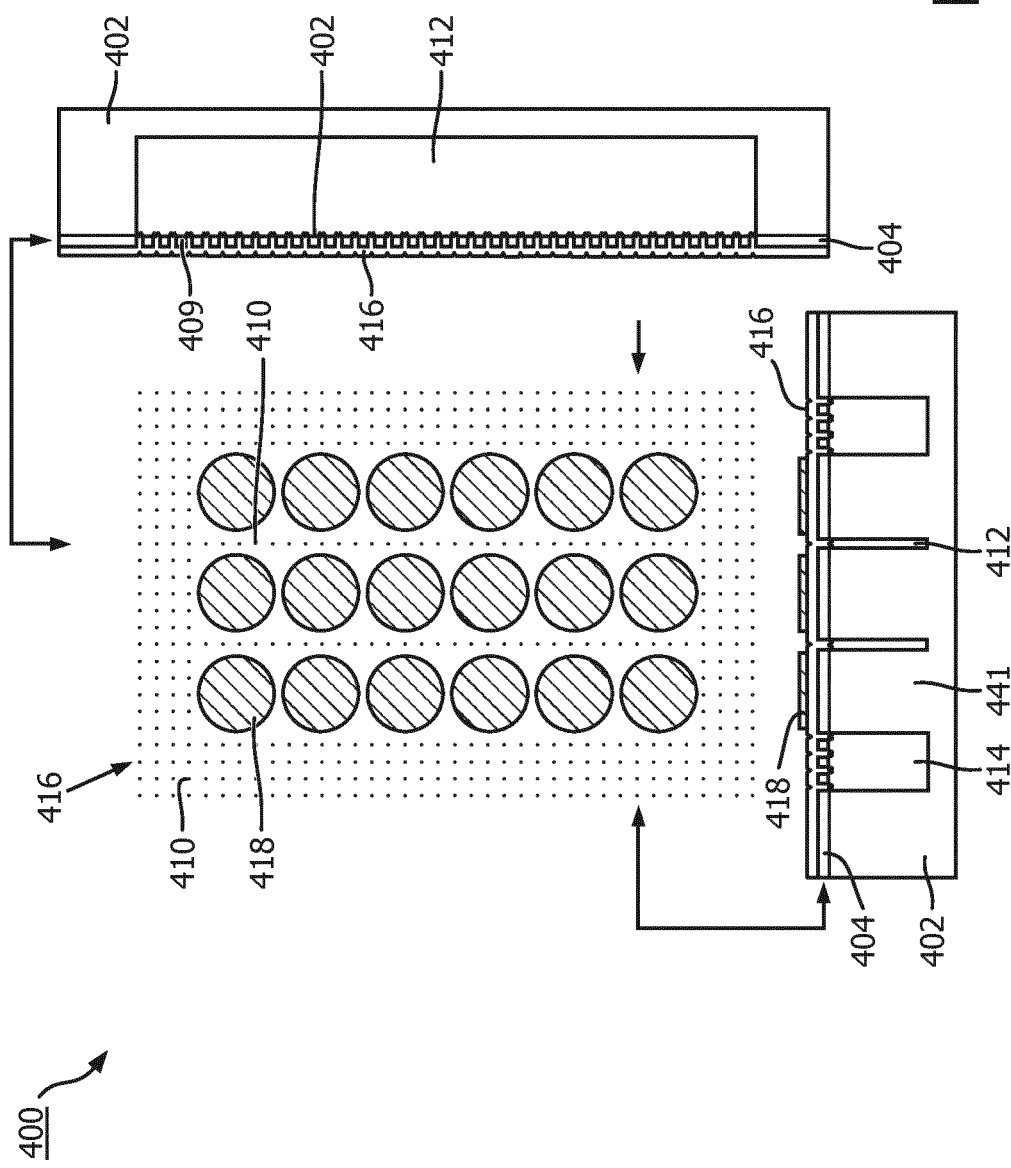
Figure 4F:
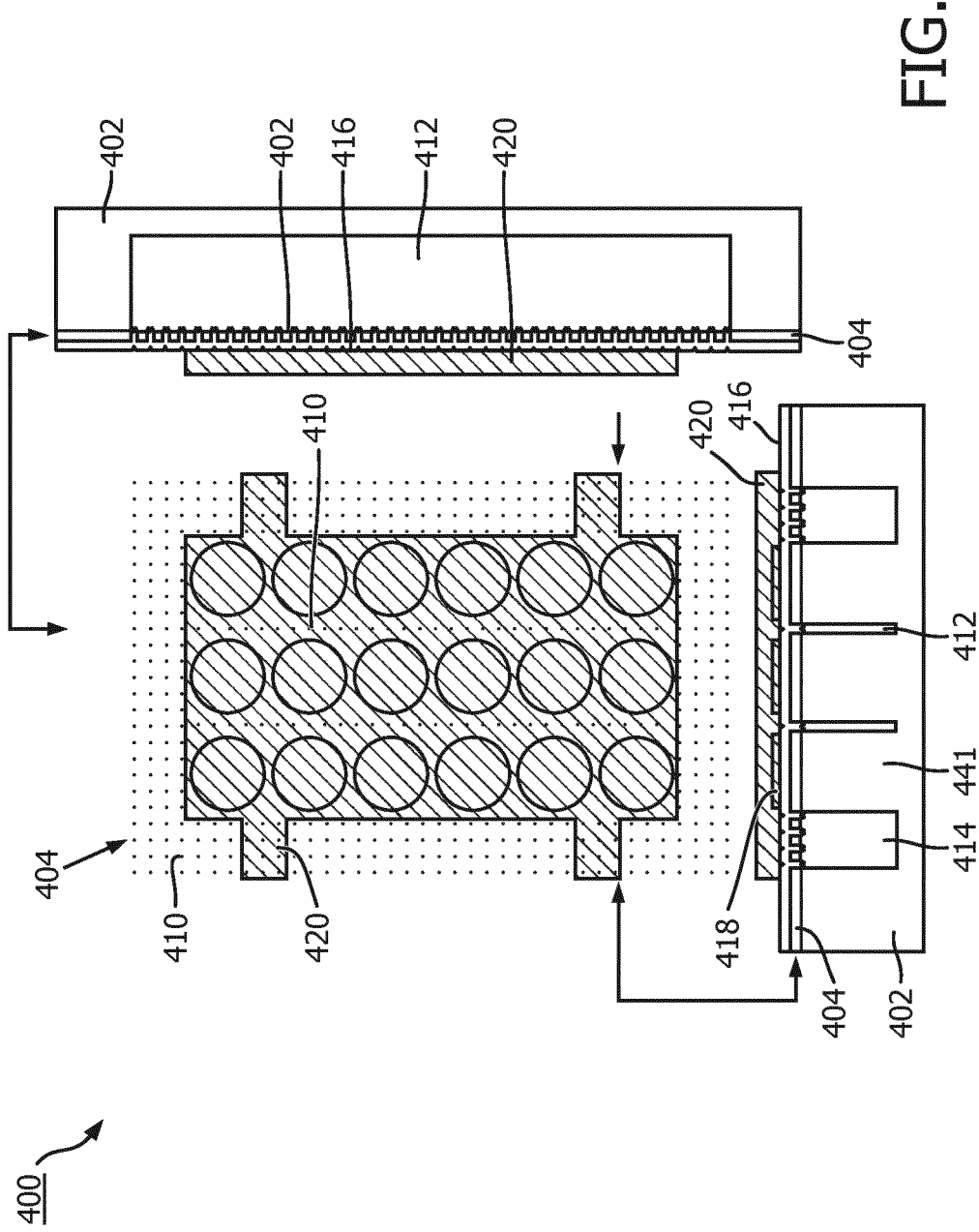
Figure 4G:
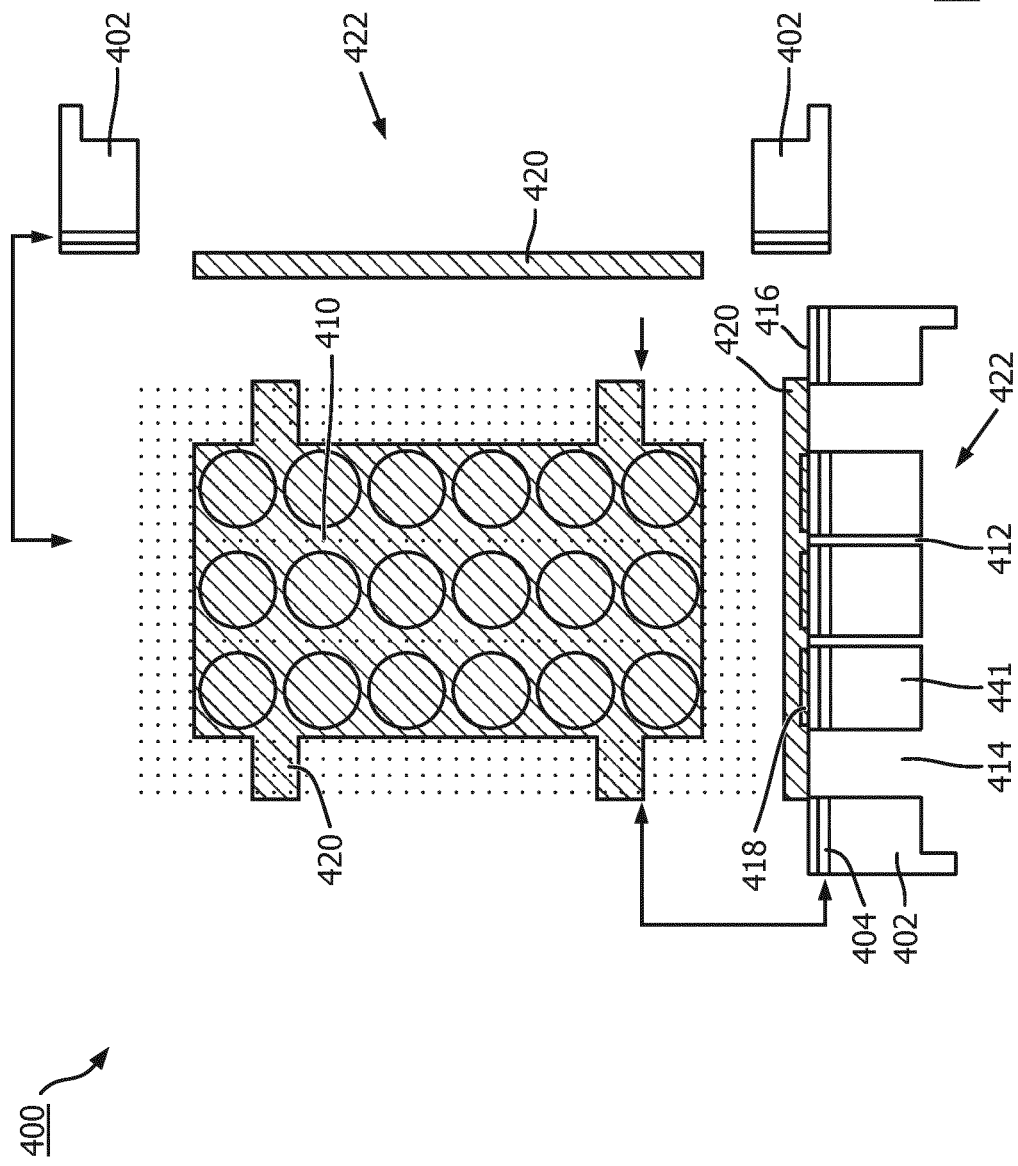

The method 300 may include further processes to form the MEMS device 400. For example, as shown in FIG. 4E, a plurality of micromachined ultrasound transducer elements 418 can be formed in the areas 406 in FIG. 4A. The transducer elements 418 can be formed in areas adjacent to areas where the trenches 412 are formed. The transducer elements 418 can be arranged in a plurality of rows extending longitudinally along the length of the scanner assembly 110 and/or the device 102. In the illustrated embodiment, each row includes a single line of transducer elements 418. Each row of transducer elements 418 and/or each island 441 can be spaced from another by the trench 412. In other embodiments, transducer elements 418 can be arranged in any other suitable configuration. For example, transducer elements 418 can be arranged in a side by side or staggered manner with a given island 441 (e.g., two or more side by side rows or staggered rows). Each island 441, with such a group of transducer elements 418, can be spaced from another island 441 with another group of transducer elements 418 by the trench 412. The trenches 412 can extend the length of the islands 441. The trenches 412 can partially and/or fully surround the islands 441 in some instances. The plurality of micromachined ultrasound transducer elements 418 can be a plurality of CMUTs or a plurality of PMUTs. For another example, as shown in FIG. 4F, after the plurality of micromachined ultrasound transducer elements 418 is formed in the areas 406, a flexible polymer layer 420 can be formed over the micromachined ultrasound transducer elements 418 and the buried trenches 412 and 414. In some implementations, electrical traces and interconnects can be fabricated in the flexible polymer layer 420 to form a flexible interconnect. In some further embodiments, as shown in FIG. 4G, the semiconductor substrate 402 can be etched from a backside to form opening 422. The opening 422 exposes the buried trenches 412 and 414 from the backside, resulting in a structure similar to the MEMS device 200 in FIG. 2F. In those embodiments, the etching from the backside of the semiconductor substrate 402 can be performed using an anisotropic etching process, such as DRIE. In some implementations, the method 300 can include removing portion of the flexible polymer layer 420 to expose the plurality of micromachined ultrasound transducer elements 418.

Figure 5A:
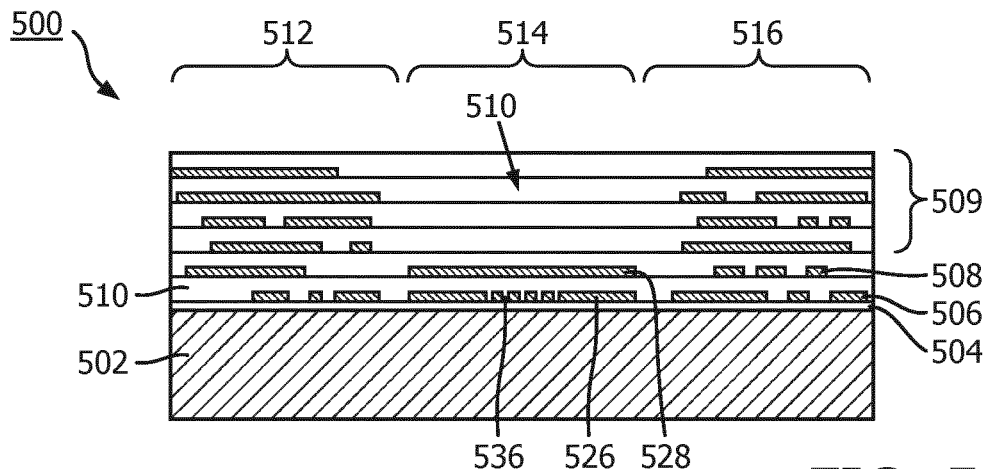
FIGS. 5A, 5B, 5C, 5D, 5E, 5F, 5G, 5H, and 5I are diagrammatic top views and cross-sectional views of a semiconductor substrate in different operations of another embodiment of the method in FIG. 3, according to an embodiment of the present disclosure.

Reference is now made to FIGS. 5A-5I, which show top views and cross-sectional views of a MEMS device 500 going through different processes in another embodiment of the method 300. Different from the MEMS device 400 in FIGS. 4A-4G, the MEMS device 500 includes active circuit elements, such as metal oxide semiconductor (MOS) transistors or an ASIC, underneath the array of MEMS components. Referring now to FIG. 5A, at block 302 of the method 300, a semiconductor substrate 502 is received. The semiconductor substrate 502 can be a silicon (Si) substrate or a germanium (Ge) substrate. In some embodiments, the semiconductor substrate 502 may include a compound semiconductor such as silicon carbide (SiC), silicon germanium (SiGe), silicon germanium carbide (SiGeC). The semiconductor substrate 502 includes a hard mask 504 thereon. In some embodiments, the hard mask 504 may be formed of silicon oxide ($SiO_2$) using chemical vapor deposition (CVD). In some implementations, the hard mask 504 may be formed of silicon nitride (SiN) or silicon oxynitride (SiON). In some instances, the hard mask 504 includes a thickness ranging between 0.5 μm and 2 μm, including, for example, 1 μm. In some implementations, the substrate 502 can be a silicon-on-insulator (SOI) substrate that includes a buried oxide (BOX). As illustrated in 5A, the semiconductor substrate 502 includes interconnect regions 512 and 516. The interconnect regions 512 and 516 are separated by a trench region 514. In the interconnect regions 512 and 516, the semiconductor substrate 502 includes a plurality of interconnect layers, such as a first metal layer 506 and a second metal layer 508 and additional metal layers 509. The additional metal layers 509 may include interconnect structures, via contacts, active components, such as complementary metal oxide semiconductor (CMOS) devices, and passive electrical components. Interlayer dielectric (ILD), such as ILD 510, separates each of the first metal layer 506, the second metal layer 508, and the metal layers 509. In the embodiments represented in FIG. 5B, in the trench region 514, the semiconductor substrate 502 includes the first and second metal layers 506 and 508, but not the additional metal layers 509. In some instances, a total height of the first metal layer 506, the second metal layer 508, the additional metal layers 509, and the ILDs 510 can be about or more than 10 μm. In those instances, forming a screen that has openings with a dimension of about 1 μm can be challenging. In the trench region 514, the semiconductor substrate 502 includes ILD 510 in place of the additional metal layer 509. The first metal layer 506 in the trench region 514 can be referred to as the first metal layer 526 and the second metal layer 508 in the trench region 514 can be referred to as the second metal layer 528. In the embodiments represented in FIG. 5A, the first metal layer 526 includes a screen pattern 536, similar to the screen in FIG. 4C. In some implementations, the screen pattern 536 can include a plurality of through holes. Each of the through holes can be substantially square in shape and includes a width/length between about 0.5 μm and about 2 μm, including, for example, about 1 μm. In these implementations, the square holes in the screen pattern 536 include a pitch that is about two times of the width/length of the hole. For example, when the width/length of each of the square hole is about 1 μm, the pitch of the square holes is about 2 μm. In some embodiments, the through holes in the screen pattern 536 can be of any shape, including circular, rectangular, triangular, polygonal, or irregular shapes.

Figure 5B:
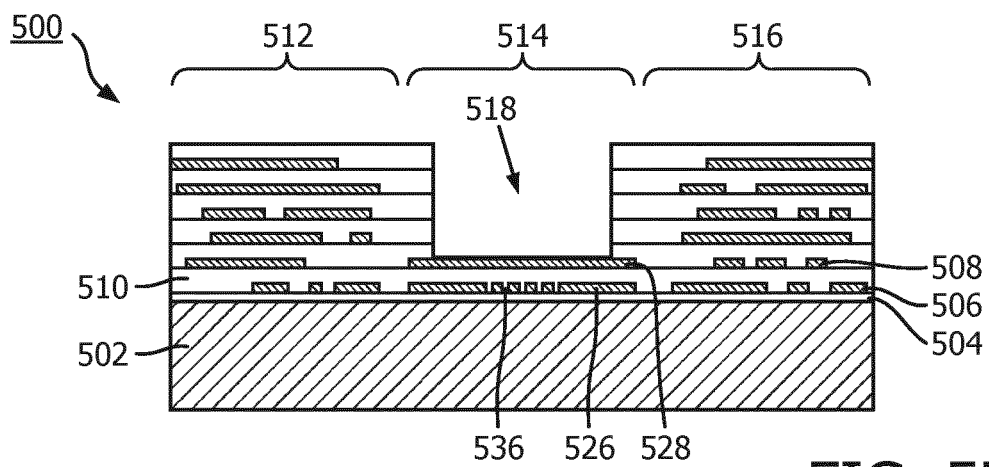
Figure 5C:
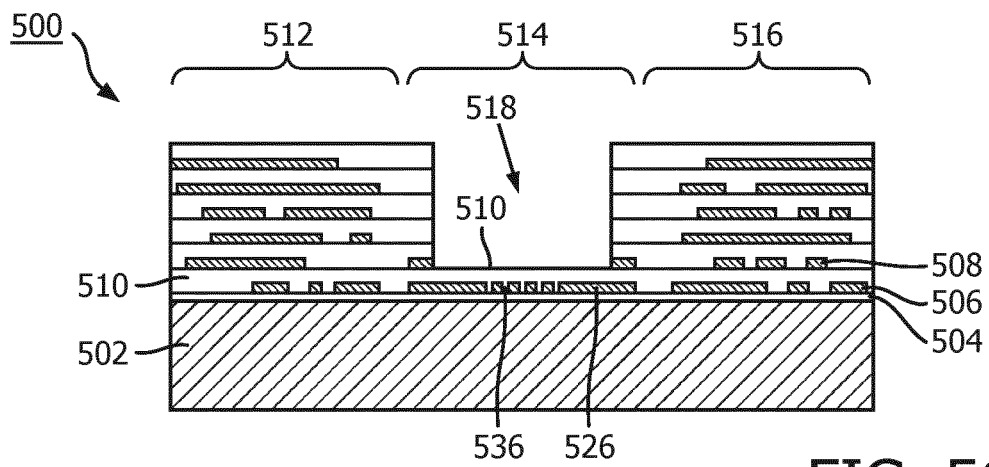
Figure 5D:
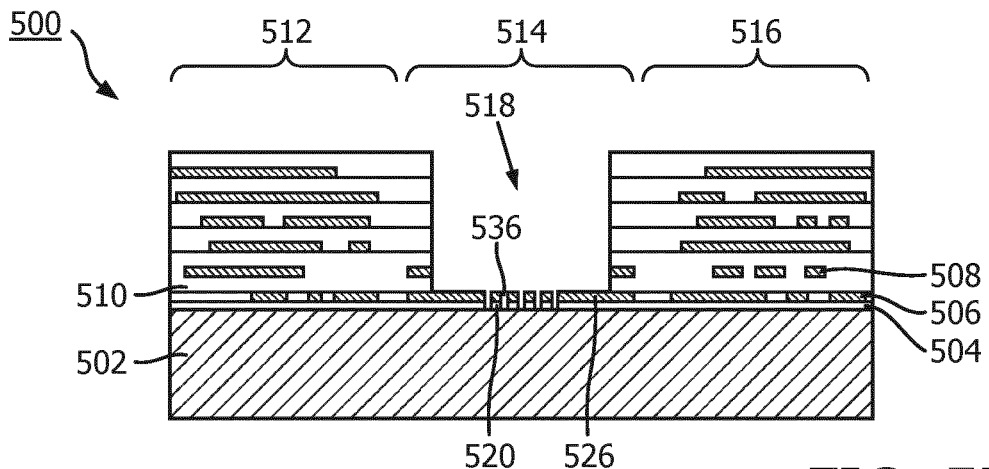
Figure 5E:
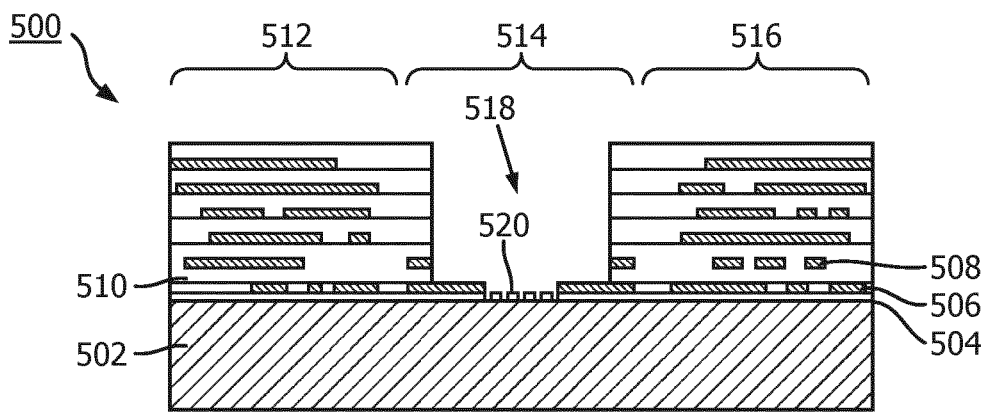

Referring now to FIGS. 5B-5E, the method 300 proceeds to block 304 where the hard mask 504 is patterned to form a screen 520 over the trench region 514. As shown in FIG. 5B, a trench 518 is formed by anisotropic etching the ILD 510 over in the trench region 514. In forming the trench 518, the second metal layer 528 in the trench region 514 can function as an etch stop layer (ESL) when the etching chemistry is selected such that the second metal layer 528 experiences a slower etching rate than the etching rate for the ILD 510. That way, the etching through the ILD 510 ion the trench region 514 can be controlled. It is noted that the second metal layer 528 in the trench region 514 can be optional and the ILD 510 in the trench region 514 can be removed without use of the second metal layer 528 as an ESL layer. Referring now to FIG. 5C, after removal of the ILD 510 in the trench region 514, the second metal layer 528 in the trench region 514 is selectively etched away by an etching chemistry that preferentially etches the second metal layer 528 without substantially etching the ILD 510. In FIG. 5D, after the second metal layer 528 in the trench region 514 is removed, the screen pattern 536 is transferred to the hard mask 504 under the first metal layer 526. The transfer of the screen pattern 536 can be transferred by anisotropically etching using an etching chemistry that preferentially etches the ILD 510 and the hard mask 504 in the trench region 514 without substantially damaging the first metal layer 526 and the screen pattern 536. The anisotropic etching can leave a screen 520 that resembles the screen pattern 536. Then, in FIG. 5E, the first metal layer 526 is removed using an etching recipe that can selectively remove the first metal layer 526 without substantially damaging the ILD 510 and the hard mask 504.

Figure 5F:
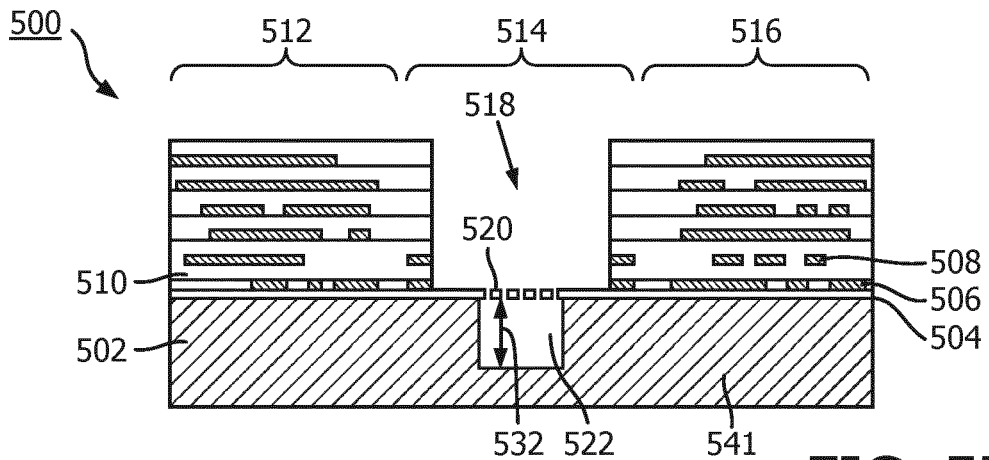

Referring now to FIG. 5F, the method 300 proceeds to block 306 where the hard mask 504 in the trench region 514 is etched using the screen 520 as an etch mask to form a trench 522. In some embodiments, the operations at block 306 are carried out using an etching chemistry that has etching selectivity with respect to the semiconductor substrate 502. That way, the material of the semiconductor substrate 502 can be selectively etched without substantially damaging the screen 520 formed of the hard mask 504. In examples where the semiconductor substrate 502 is a silicon substrate and the hard mask 504 is formed of silicon oxide, the operations at block 306 are performed using a DRIE process that preferentially etches the silicon substrate 502 exposed by the screen 520 without substantially damaging the screen formed of silicon oxide. In some embodiments, a cycle time for etch cycles of the DRIE process can be increased to increase the undercut, so as to etch the semiconductor substrate 502 directly under the screen 520. The operations of block 306 create the trench 522 that is buried or positioned under the screen 520. The trench 522 can include a depth 532. In some instances, the depth 532 can be between about 30 μm and 50 μm, including, for example, about 40 μm. In case an SOI substrate is used, the depth of the trench is equal to the thickness of the top silicon layer of the SOI substrate. The trench 522 defines the islands 541 of the substrate 502. The islands 541 are spaced apart and/or separated by the trench 522.

Figure 5G:
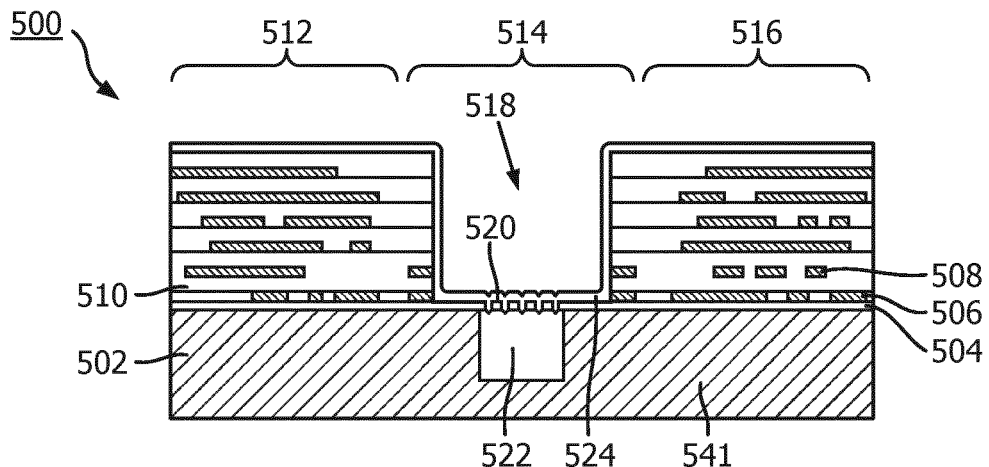

Referring now to FIG. 5G, the method 300 proceeds to block 308 where a material layer 524 is deposited over the screen 520. In some embodiments, the material layer 524 is formed over the screen 520 using a process that does not fill the trench 522 with the material layer 524. In some implementations, the material layer 524 can be a silicon oxide layer deposited using plasma-enhanced chemical vapor deposition (PECVD) to close the holes in the screen 520. Put differently, the operations at block 308 lay the material layer 524 over the screen 520 to completely cover the trench 522 without filling the trench 522. The operations at block 308 therefore leave trench 522 buried under the screen 520 and the material layer 524.

Figure 5H:
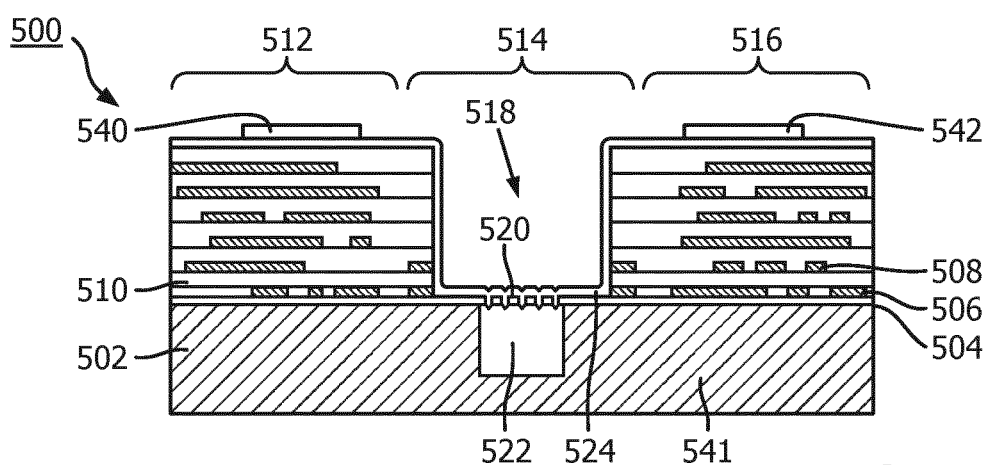
Figure 5I:
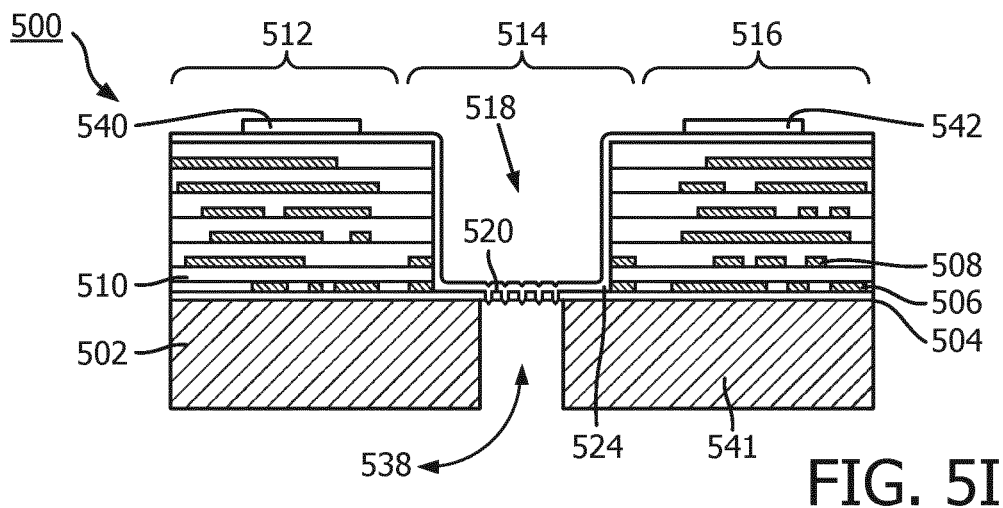

The method 300 may include further processes to form the MEMS device 500. For example, as shown in FIG. 5H, micromachined ultrasound transducer elements 540 and 542 can be formed over the interconnect regions 512 and 516. In some implementations, the material layer 524 deposited in the interconnect regions 512 and 516 can be removed by planarization techniques, such as CMP, before the micromachined ultrasound transducer elements 540 and 542 are formed in the interconnect region. In some embodiments, the micromachined ultrasound transducer elements 540 and 542 can be capacitive micromachined ultrasound transducer elements (CMUTs) or piezoelectric micromachined ultrasound transducer (PMUT). In some implementations, electrical traces and interconnects can be fabricated in the flexible polymer layer to form a flexible interconnect. In some further embodiments shown in FIG. 5I, the semiconductor substrate 502 can be etched from a backside to form opening 538. The opening 538 exposes the buried trench 522 in FIG. 5G from the backside, resulting in a structure similar to the MEMS device 200 in FIG. 2F. In those embodiments, the etching from the backside of the semiconductor substrate 502 can be performed using an anisotropic etching process, such as DRIE. In some embodiments, before the opening 538 is formed in the semiconductor substrate 502, a flexible polymer layer can be formed over the interconnect regions 512 and 516 and the trench region 514, including over the buried trench 522 covered by the material layer 524 and the micromachined ultrasound transducer elements 540 and 542.

Figure 6:
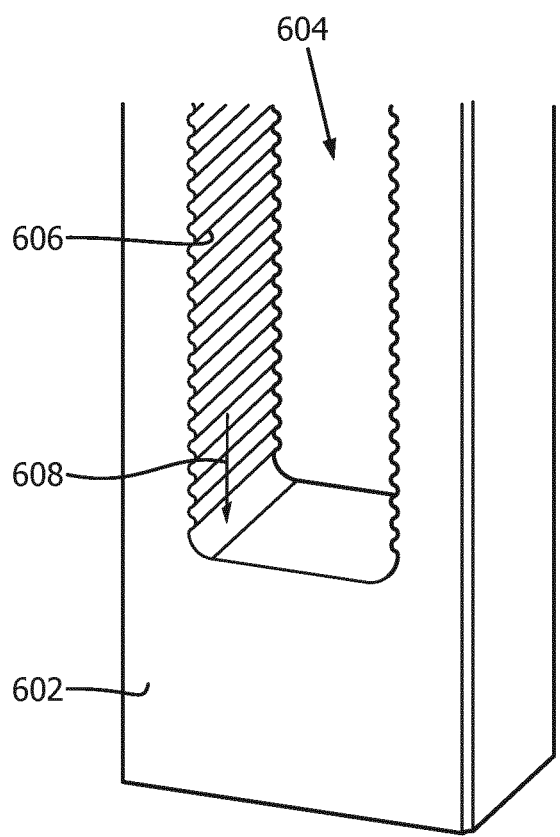
FIG. 6 is a scanning electron microscope (SEM) image of a trench formed using deep reactive ion etching (DRIE), according to aspects of the present disclosure.

Etching a semiconductor substrate by DRIE using a screen as the etch mask to form buried trenches, such as trenches 412 and 414 in FIG. 4C or trench 522 in FIG. 5F, can generate unique structures on the sidewalls of the buried trenches. Referring now to FIG. 6, shown therein is a scanning electron microscope (SEM) image of a trench 604 formed in a semiconductor substrate 602 without using a screen as an etch mask. When the trench 604 is anisotropically etched using deep reactive ion etching (DRIE), a uni-directional wave-like surface 606 can be observed. The uni-directional wave-like surface 606 includes wave-like structures propagating along a direction 608, which is parallel to the etching direction of the DRIE.

Figure 7A:
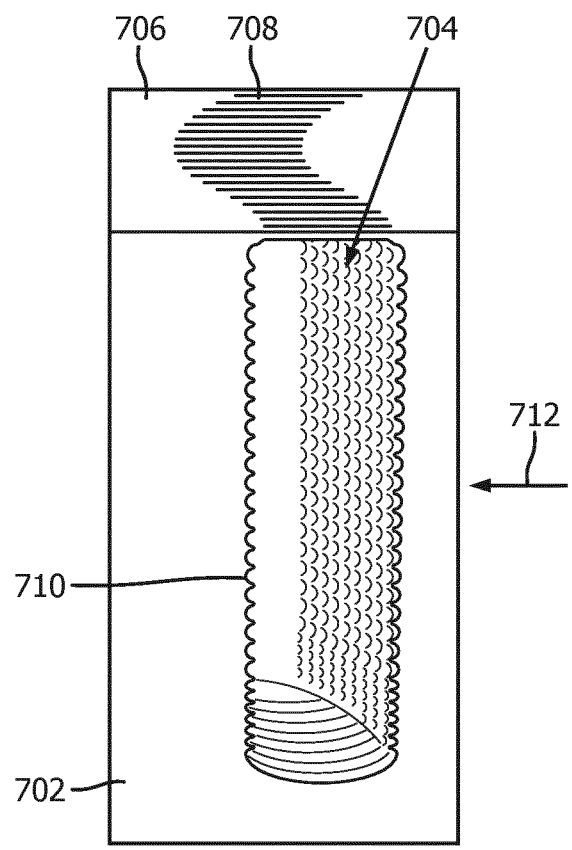
FIGS. 7A and 7B are SEM images of a buried trench formed using DRIE according to embodiments of the present disclosure.
Figure 7B:
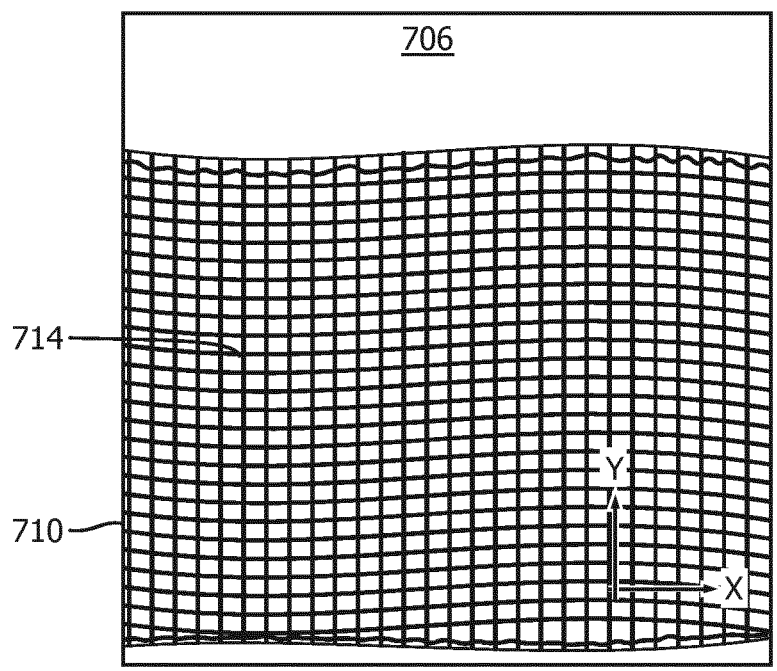

When a screen, such as those described herein, is used as an etch mask, the patterns on sidewalls of the trench change. Referring now to FIG. 7A, shown therein is a SEM image of a buried trench 704 formed in a semiconductor substrate 702 using a screen 708 formed in a hard mask layer 706. Similar to the embodiments shown in FIGS. 4A-4G or FIGS. 5A-5I, the semiconductor substrate 702 can be a silicon substrate and the hard mask layer 706 can be a silicon oxide layer. FIG. 7B shows a SEM image of the sidewall 710 of the buried trench 704 viewed from a direction 712. As illustrated in FIG. 7B, the sidewall 710 can include a bi-directional wave-like surface 714. The bi-directional wave-like surface 714 includes wave-like structures that propagate along the X direction as well as the Y direction perpendicular to the X direction. In some instances, the uni-directional wave-like surface 606 can be referred to as single scallops and the bi-directional wave-like surface 714 can be referred to as double scallops. The bi-directional wave-like surface 714 on the sidewall 710 is present at the end of the manufacturing process. The surface 714 provides an indication after manufacturing is complete that the trenches were formed by etching through a screen in the hard mask layer, as described herein, without etching completely through the hard mask layer.

Figure 8A:
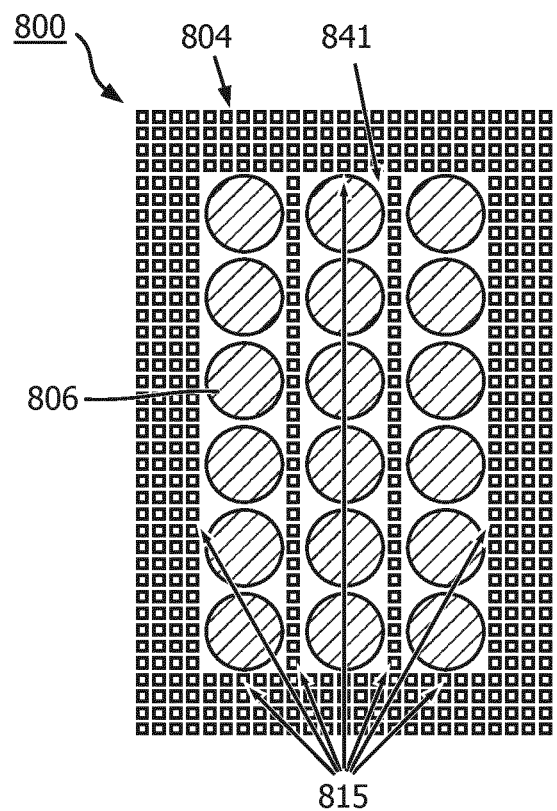
FIGS. 8A and 8B are diagrammatic top views of a semiconductor substrate with different sidewall configurations according to embodiments of the present disclosure.
Figure 8B:
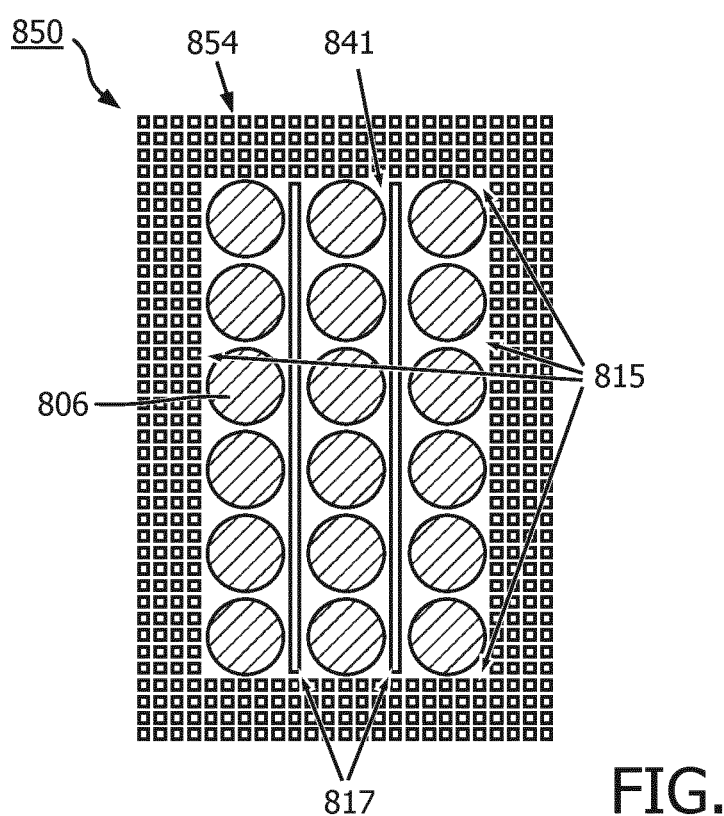

FIGS. 8A and 8B are diagrammatic top views of a semiconductor substrate with different substrate sidewall configurations according to embodiments of the present disclosure. The substrate is separated into spaced-apart segments 841, each having multiple sidewalls. Generally, at least one sidewall of a substrate island 841 with ultrasound transducer elements 806 (or areas therefor) includes the two-directional wave-like features described in FIGS. 7A and 7B. The hard mask layer 804 of the MEMS device 800 in FIG. 8A includes connections points 810 between the hard mask and the substrate islands 841. The two-directional wave-like features occur along the sidewalls of the substrate below the connection points 810 of the hard mask to the substrate islands 841. In the embodiment of FIG. 8A, all four sidewalls of each island 841 includes the connection points 810 and thus the two-directional wave-like features as well.

The hard mask layer 854 of the MEMS device 850 includes openings 817 in the form of a single slit. The sidewalls of the substrate below the single slit 817 include the uni-directional wave-like features described in FIG. 6. The hard mask layer 854 also includes the connection points 810 of the hard mask to the substrate islands 841. The two-directional wave-like features (FIGS. 7A and 7B) occur along the sidewalls of the substrate below the connection points 810. Accordingly, in the embodiment of FIG. 8B, one or more sidewalls of each island 841 include uni-directional wave-like features, and one or more sidewalls of the each island 841 include the two-directional wave-like features.

Thus, the present disclosure provides a method of forming a buried trench in a semiconductor substrate and a MEMS device fabricated using the method. By eliminating the use of a sacrificial polymer material, the embodiments of the present disclosure advantageously improve the yield and enlarge the process window of forming buried trenches in MEMS devices. Besides fabrication of MEMS devices such as ultrasound transducer arrays, the embodiments of the present disclosure can be applied to microfluidics, to create well-defined micro channels in, e.g., a silicon substrate. Persons skilled in the art will recognize that the apparatus, systems, and methods described above can be modified in various ways. Accordingly, persons of ordinary skill in the art will appreciate that the embodiments encompassed by the present disclosure are not limited to the particular embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging device, comprising:
   a flexible elongate member configured to be positioned within a body lumen of a patient, the flexible elongate member comprising a proximal portion and a distal portion; and
   an ultrasound imaging assembly disposed at the distal portion of the flexible elongate member, the ultrasound imaging assembly configured to obtain imaging data of the body lumen, the ultrasound imaging assembly comprising a transducer array comprising:
      a substrate separated by a trench into a plurality of spaced-apart segments,
      a hard mask layer disposed over the substrate, wherein a first area of the hard mask layer comprises a first plurality of holes such that the first area of the hard mask layer is formed into a screen aligned with the trench, and
      a row of transducer elements disposed on a second area of the hard mask layer.

2. The intraluminal ultrasound imaging device of claim 1, wherein the substrate comprises silicon,
   wherein the hard mask layer comprises silicon oxide.

3. The intraluminal ultrasound imaging device of claim 1, wherein the row of transducer elements comprises capacitive micromachined ultrasound transducer (CMUT) elements or piezoelectric micromachined ultrasound transducer (PMUT) elements.

4. The intraluminal ultrasound imaging device of claim 1, wherein the ultrasound imaging assembly further comprises a flexible interconnect and a further row of transducer elements,
   wherein the row of transducer elements and the further row of transducer elements are spaced apart from one another by a trench,
   wherein the flexible interconnect spans over the trench, and
   wherein the flexible interconnect comprises a surface including an array of recesses.

5. The intraluminal ultrasound imaging device of claim 4, further comprising:
   a tubular member, wherein the flexible interconnect and the transducer array positioned around the tubular member.

6. A method of manufacturing an intraluminal ultrasound imaging device, comprising:
   providing a substrate comprising a hard mask on a first side of the substrate;
   forming a first area of the hard mask into a screen by providing a first plurality of holes through the hard mask in the first area;
   etching the substrate through the first plurality of holes, thereby forming a trench aligned with the screen;
   depositing a material layer over first plurality of holes;
   forming a row of ultrasound transducer elements on a second area of the hard mask adjacent to the first area; and
   forming a flexible layer over the hard mask in the first and second areas.

7. The method of claim 6, wherein the substrate is a silicon-on-insulator (SOI) substrate.

8. The method of claim 6, wherein providing the substrate comprises forming the hard mask on the first side of the substrate.

9. The method of claim 6, wherein forming the first area of the hard mask in the screen comprises etching the hard mask using a metal layer as an etch mask, the metal layer including a second plurality of holes.

10. The method of claim 6, wherein etching the substrate through the first plurality of holes comprises etching the substrate through the first plurality of holes using deep reactive ion etching (DRIE).

11. The method of claim 6, wherein depositing the material layer over the first plurality of holes comprises depositing the material layer using plasma-enhanced chemical vapor deposition (PECVD).

12. The method of claim 6, wherein forming the plurality of ultrasound transducer elements on the second area of the hard mask comprises forming capacitive micromachined ultrasound transducer (CMUT) elements or piezoelectric micromachined ultrasound transducer (PMUT) elements.

13. The method of claim 6, further comprising:
   forming an opening on a second side of the substrate to expose the trench.

14. The method of claim 13, further comprising:
   removing, from the second side through the opening, the material layer and the hard mask exposed in the trench.

15. The method of claim 6, further comprising planarizing the material layer deposited over the first plurality of holes.

16. An intraluminal ultrasound imaging device, comprising:
   a flexible elongate member configured to be positioned within a body lumen of a patient, the flexible elongate member comprising a proximal portion and a distal portion; and
   an ultrasound imaging assembly disposed at the distal portion of the flexible elongate member, the ultrasound imaging assembly configured to obtain imaging data of the body lumen, the ultrasound imaging assembly comprising a transducer array comprising:

a substrate, a silicon oxide layer disposed over the substrate, and a plurality of rows of micromachined ultrasound transducer elements disposed on the silicon oxide layer, wherein two of the plurality of rows of micromachined ultrasound transducer elements are spaced apart by a trench formed by etching through a screen aligned with the trench, wherein a first area of the silicon oxide layer is formed into the screen by a plurality of holes provided through the silicon oxide layer in the first area, wherein the plurality of rows of micromachined ultrasound transducer elements is disposed on a second area of the silicon oxide layer adjacent to the first area.

17. The intraluminal ultrasound imaging device of claim 1, wherein a first sidewall of each of the plurality of spaced-apart segments comprises wave-like features propagating along two directions perpendicular to one another.

18. The intraluminal ultrasound imaging device of claim 17, wherein a different, second sidewall of each of the plurality of spaced-apart segments of the substrate comprises wave-like features propagating along only one of the two directions.

\* \* \* \* \*